(12) United States Patent
Jones et al.

(10) Patent No.: US 9,610,416 B2
(45) Date of Patent: Apr. 4, 2017

(54) FLOW GENERATOR CHASSIS ASSEMBLY WITH SUSPENSION SEAL

(71) Applicant: ResMed Limited, Bella Vista, New South Wales (AU)

(72) Inventors: Richard Llewelyn Jones, Sydney (AU); Saad Nasr, Sydney (AU); Joern Lange, Sydney (AU); Ernie Wei-Chih Tsai, Sydney (AU); Barton John Kenyon, Sydney (AU); Geoffrey Crumblin, Sydney (AU)

(73) Assignee: ResMed Limited, Bella Vista (AU)

( * ) Notice: Subject to any disclaimer, the term of this patent is extended or adjusted under 35 U.S.C. 154(b) by 0 days.

(21) Appl. No.: 14/556,343

(22) Filed: Dec. 1, 2014

(65) Prior Publication Data

US 2015/0083132 A1    Mar. 26, 2015

Related U.S. Application Data

(63) Continuation of application No. 12/794,206, filed on Jun. 4, 2010, now Pat. No. 8,931,481.

(Continued)

(51) Int. Cl.
   *A61M 16/00* (2006.01)
   *F04D 29/42* (2006.01)
   (Continued)

(52) U.S. Cl.
   CPC .... *A61M 16/0066* (2013.01); *A61M 16/0003* (2014.02); *A61M 16/105* (2013.01);
   (Continued)

(58) Field of Classification Search
   CPC .......... A61M 16/00; A61M 2016/0069; A61M 16/06; A61M 2016/0039;
   (Continued)

(56) References Cited

U.S. PATENT DOCUMENTS

| 1,085,833 A | 2/1914 | Wilson |
| 1,974,843 A | 9/1934 | Blashfield |

(Continued)

FOREIGN PATENT DOCUMENTS

| AU | 200065475 B2 | 4/2001 |
| DE | 275612 | 1/1913 |

(Continued)

OTHER PUBLICATIONS

Petition for *Inter Partes* Review of U.S. Pat. No. Re. 44,453, *BMC Medical Co. Ltd.*, Petitioner v. *ResMed Limited*, Patent Owner, Case No. IPR2014-01363, Aug. 22, 2014, 66 pages.

(Continued)

*Primary Examiner* — Peter S Vasat
*Assistant Examiner* — Mark Wardas
(74) *Attorney, Agent, or Firm* — Nixon & Vanderhye P.C.

(57) ABSTRACT

A seal is provided for a chassis assembly of a flow generator configured to provide a flow of breathable gas. The chassis assembly includes an upper chassis and a lower chassis. The seal includes a blower receptacle sealing portion configured to seal a blower receptacle of the chassis assembly configured to receive a blower configured to generate the flow of breathable gas; a flow sensor sealing portion configured to seal a flow sensor provided in the chassis assembly and configured to measure the flow of breathable gas; a blower mount configured to receive a portion of the blower and mount the blower to the seal; and a blower mount suspension configured to connect the blower mount to the blower receptacle sealing portion, wherein in an assembled condition the seal and the chassis assembly define a flow path from an inlet of the chassis assembly to the blower receptacle of the chassis assembly to an outlet of the chassis assembly. A flow generator for generating a flow of breathable gas includes a chassis assembly comprising a lower (Continued)

chassis and an upper chassis, the lower chassis and the upper chassis defining a blower receptacle; a blower provided in the blower receptacle; and the seal.

36 Claims, 19 Drawing Sheets

Related U.S. Application Data

(60) Provisional application No. 61/184,124, filed on Jun. 4, 2009.

(51) Int. Cl.
  *F04D 29/60* (2006.01)
  *A61M 16/10* (2006.01)
(52) U.S. Cl.
  CPC ....... *F04D 29/4226* (2013.01); *F04D 29/601* (2013.01); *A61M 2016/003* (2013.01); *A61M 2016/0027* (2013.01); *A61M 2205/3334* (2013.01); *A61M 2205/3368* (2013.01); *A61M 2205/42* (2013.01); *A61M 2205/75* (2013.01); *Y10T 29/49826* (2015.01)
(58) Field of Classification Search
  CPC ...... A61M 2016/0021; A61M 16/0066; A61M 16/0003; A61M 16/105; A61M 2205/3334; A61M 2205/75; A61M 2016/003; A61M 2205/42; A61M 2016/0027; A61M 2205/3368; F04B 39/127; F04B 39/0044; F04B 35/045; A47L 9/22; F25B 31/02; F04D 29/601; F04D 29/4226; F04D 29/624; F04D 29/626; Y10T 29/49826
  USPC ............ 128/200.24, 204.14, 204.17, 204.18, 128/204.21, 205.18, 202.27, 423.14, 128/214.1; 417/423.11, 423.14, 363; 248/638, 634; 415/119, 214.1
  See application file for complete search history.

(56) References Cited

U.S. PATENT DOCUMENTS

| | | |
|---|---|---|
| RE19,826 E | 1/1936 | Aisenstein |
| 2,220,669 A | 11/1940 | Allen |
| 2,603,157 A | 7/1952 | Conery |
| 2,780,708 A | 2/1957 | Glynn et al. |
| 2,793,506 A | 6/1957 | Moody |
| 2,945,619 A | 7/1960 | Ballard |
| 3,171,353 A | 3/1965 | McMahan |
| 3,316,910 A | 5/1967 | Davis |
| 3,584,401 A | 6/1971 | Cryer et al. |
| 3,612,710 A | 10/1971 | Mount |
| 3,620,638 A | 11/1971 | Kaye et al. |
| 3,638,926 A | 2/1972 | Melville et al. |
| 3,659,604 A | 5/1972 | Melville et al. |
| 3,690,317 A | 9/1972 | Millman |
| 3,806,102 A | 4/1974 | Valenta et al. |
| 3,864,440 A | 2/1975 | Giocoechea |
| 3,954,920 A | 5/1976 | Heath |
| 4,037,994 A | 7/1977 | Bird |
| 4,051,205 A | 9/1977 | Grant |
| 4,105,372 A | 8/1978 | Mishina et al. |
| 4,171,190 A | 10/1979 | Hudson |
| 4,222,971 A | 9/1980 | Eilert |
| 4,229,142 A | 10/1980 | Le Dall et al. |
| 4,237,080 A | 12/1980 | Elliott |
| 4,243,396 A | 1/1981 | Cronenberg |
| 4,336,798 A | 6/1982 | Beran |
| 4,383,800 A | 5/1983 | Becker et al. |
| 4,502,481 A | 3/1985 | Christian |
| 4,523,896 A | 6/1985 | Lhenry et al. |
| 4,532,088 A | 7/1985 | Miller |
| 4,576,616 A | 3/1986 | Mottram et al. |
| 4,588,425 A | 5/1986 | Usry et al. |
| 4,621,632 A | 11/1986 | Bartels et al. |
| 4,657,713 A | 4/1987 | Miller |
| 4,686,354 A | 8/1987 | Makin |
| 4,753,758 A | 6/1988 | Miller |
| 4,799,287 A | 1/1989 | Belanger |
| 4,802,819 A | 2/1989 | Bevington |
| 4,807,616 A | 2/1989 | Adahan |
| 4,838,258 A | 6/1989 | Dryden et al. |
| 4,906,417 A | 3/1990 | Gentry |
| 4,913,140 A | 4/1990 | Orec et al. |
| 4,913,951 A | 4/1990 | Pitolaj |
| 4,921,642 A | 5/1990 | LaTorraca |
| 4,926,856 A | 5/1990 | Cambio et al. |
| 4,929,149 A | 5/1990 | Greenspan |
| 4,941,469 A | 7/1990 | Adahan |
| 4,946,348 A | 8/1990 | Yapp |
| 4,953,546 A | 9/1990 | Blackmer et al. |
| 4,973,234 A | 11/1990 | Swenson |
| 4,993,411 A | 2/1991 | Callaway |
| 5,097,424 A | 3/1992 | Ginevri et al. |
| 5,127,800 A | 7/1992 | Hyll et al. |
| 5,199,009 A | 3/1993 | Svast |
| 5,199,846 A | 4/1993 | Fukasaku et al. |
| 5,231,979 A | 8/1993 | Rose et al. |
| 5,237,987 A | 8/1993 | Anderson et al. |
| 5,271,391 A | 12/1993 | Graves |
| 5,329,939 A | 7/1994 | Howe |
| 5,391,063 A | 2/1995 | Hantle et al. |
| 5,443,061 A | 8/1995 | Champain et al. |
| 5,445,143 A | 8/1995 | Sims |
| 5,474,112 A | 12/1995 | Carola |
| 5,482,031 A | 1/1996 | Lambert |
| 5,537,997 A | 7/1996 | Mechlenburg et al. |
| 5,558,084 A | 9/1996 | Daniell et al. |
| 5,564,415 A | 10/1996 | Dobson et al. |
| 5,577,496 A | 11/1996 | Blackwood et al. |
| 5,588,423 A | 12/1996 | Smith |
| 5,598,837 A | 2/1997 | Sirianne, Jr. et al. |
| 5,651,775 A | 7/1997 | Walker et al. |
| 5,655,522 A | 8/1997 | Mechlenburg et al. |
| 5,673,687 A | 10/1997 | Dobson et al. |
| 5,794,219 A | 8/1998 | Brown |
| 5,822,715 A | 10/1998 | Worthington et al. |
| 5,828,943 A | 10/1998 | Brown |
| 5,832,448 A | 11/1998 | Brown |
| 5,848,592 A | 12/1998 | Sibley |
| 5,870,283 A | 2/1999 | Maeda et al. |
| 5,879,163 A | 3/1999 | Brown et al. |
| 5,887,133 A | 3/1999 | Brown et al. |
| 5,888,053 A | 3/1999 | Kobayashi et al. |
| 5,897,493 A | 4/1999 | Brown |
| 5,899,855 A | 5/1999 | Brown |
| 5,913,310 A | 6/1999 | Brown |
| 5,916,493 A | 6/1999 | Miller et al. |
| 5,918,603 A | 7/1999 | Brown |
| 5,933,136 A | 8/1999 | Brown |
| 5,940,801 A | 8/1999 | Brown |
| 5,943,473 A | 8/1999 | Levine |
| 5,951,300 A | 9/1999 | Brown |
| 5,956,501 A | 9/1999 | Brown |
| 5,960,403 A | 9/1999 | Brown |
| 5,985,559 A | 11/1999 | Brown |
| 5,997,476 A | 12/1999 | Brown |
| D419,658 S | 1/2000 | Matchett et al. |
| 6,023,686 A | 2/2000 | Brown |
| 6,032,119 A | 2/2000 | Brown et al. |
| 6,050,260 A | 4/2000 | Daniell et al. |
| 6,101,478 A | 8/2000 | Brown |
| 6,109,865 A | 8/2000 | Ishikawa |
| 6,123,082 A | 9/2000 | Berthon-Jones |
| 6,129,524 A | 10/2000 | Wollenweber et al. |
| 6,131,571 A | 10/2000 | Lampotang et al. |
| 6,135,432 A | 10/2000 | Hebblewhite et al. |
| 6,144,837 A | 11/2000 | Quy |
| 6,152,132 A | 11/2000 | Psaros |

(56) References Cited

U.S. PATENT DOCUMENTS

| | | | |
|---|---|---|---|
| 6,158,978 A | 12/2000 | Norbury, Jr. | |
| 6,161,095 A | 12/2000 | Brown | |
| 6,185,095 B1 | 2/2001 | Helot et al. | |
| 6,189,870 B1 | 2/2001 | Withall | |
| 6,202,991 B1 | 3/2001 | Coniglio et al. | |
| 6,210,116 B1 | 4/2001 | Kuczaj et al. | |
| 6,213,119 B1 | 4/2001 | Brydon et al. | |
| 6,216,691 B1 * | 4/2001 | Kenyon et al. | 128/205.18 |
| 6,231,052 B1 | 5/2001 | Forlander | |
| 6,257,171 B1 | 7/2001 | Rivard | |
| 6,279,574 B1 | 8/2001 | Richardson et al. | |
| 6,308,706 B1 | 10/2001 | Lammers et al. | |
| 6,315,526 B1 | 11/2001 | Jones | |
| 6,332,462 B1 | 12/2001 | Krohn | |
| 6,338,473 B1 | 1/2002 | Hebblewhite et al. | |
| 6,340,288 B1 | 1/2002 | Hulkkonen et al. | |
| 6,349,724 B1 | 2/2002 | Burton et al. | |
| D454,393 S | 3/2002 | Lynch et al. | |
| 6,386,845 B1 * | 5/2002 | Bedard | 417/423.15 |
| 6,397,841 B1 | 6/2002 | Kenyon et al. | |
| 6,398,197 B1 | 6/2002 | Dickinson | |
| 6,435,180 B1 | 8/2002 | Hewson et al. | |
| 6,471,493 B2 | 10/2002 | Choi et al. | |
| D467,335 S | 12/2002 | Lithgow et al. | |
| D468,011 S | 12/2002 | Lynch et al. | |
| D468,017 S | 12/2002 | McCombs | |
| 6,514,053 B2 | 2/2003 | Takura et al. | |
| 6,543,449 B1 | 4/2003 | Woodring et al. | |
| 6,554,260 B1 | 4/2003 | Lipscombe et al. | |
| 6,591,834 B1 | 7/2003 | Colla et al. | |
| 6,604,390 B1 | 8/2003 | Nooner | |
| 6,615,444 B2 | 9/2003 | McGill et al. | |
| 6,622,724 B1 | 9/2003 | Truitt et al. | |
| 6,655,207 B1 * | 12/2003 | Speldrich et al. | 73/202.5 |
| 6,672,300 B1 | 1/2004 | Grant | |
| D487,311 S | 3/2004 | Lithgow et al. | |
| 6,718,974 B1 | 4/2004 | Moberg | |
| D493,520 S | 7/2004 | Bertinetti et al. | |
| D493,884 S | 8/2004 | Virr et al. | |
| 6,772,999 B2 | 8/2004 | Lipscombe et al. | |
| 6,775,882 B2 | 8/2004 | Murphy et al. | |
| D498,527 S | 11/2004 | Virr et al. | |
| 6,827,340 B2 | 12/2004 | Austin et al. | |
| 6,837,260 B1 * | 1/2005 | Kuehn | 137/315.01 |
| 6,874,771 B2 | 4/2005 | Birdsell et al. | |
| 6,896,478 B2 | 5/2005 | Botros et al. | |
| 6,910,483 B2 | 6/2005 | Daly et al. | |
| 6,918,389 B2 | 7/2005 | Seakins et al. | |
| 6,935,337 B2 | 8/2005 | Virr et al. | |
| 7,096,864 B1 | 8/2006 | Mayer et al. | |
| 7,111,624 B2 | 9/2006 | Thudor et al. | |
| 7,137,388 B2 | 11/2006 | Virr et al. | |
| 7,225,809 B1 | 6/2007 | Bowen et al. | |
| 7,413,173 B2 | 8/2008 | DiMatteo et al. | |
| 7,571,725 B2 | 8/2009 | Wickham et al. | |
| 7,614,398 B2 | 11/2009 | Virr et al. | |
| 7,616,871 B2 | 11/2009 | Kramer | |
| 7,677,246 B2 | 3/2010 | Kepler et al. | |
| 7,891,573 B2 | 2/2011 | Finkam et al. | |
| 7,909,032 B2 | 3/2011 | Feldhahn et al. | |
| 7,967,576 B2 | 6/2011 | Abate et al. | |
| 8,051,852 B2 | 11/2011 | Bassin | |
| RE44,453 E | 8/2013 | Virr et al. | |
| 8,517,012 B2 | 8/2013 | Daly | |
| 2002/0020930 A1 | 2/2002 | Austin et al. | |
| 2002/0022973 A1 | 2/2002 | Sun et al. | |
| 2002/0056453 A1 | 5/2002 | Klopp et al. | |
| 2002/0159897 A1 | 10/2002 | Kegg et al. | |
| 2003/0062045 A1 | 4/2003 | Woodring et al. | |
| 2003/0084900 A1 | 5/2003 | LeClerc et al. | |
| 2003/0115085 A1 | 6/2003 | Satoh | |
| 2003/0168064 A1 | 9/2003 | Daly et al. | |
| 2003/0208465 A1 | 11/2003 | Yurko et al. | |
| 2003/0230308 A1 | 12/2003 | Linden | |
| 2004/0035422 A1 | 2/2004 | Truitt et al. | |
| 2004/0055597 A1 | 3/2004 | Virr et al. | |
| 2004/0060559 A1 | 4/2004 | Virr et al. | |
| 2005/0005937 A1 | 1/2005 | Farrugia et al. | |
| 2005/0103339 A1 | 5/2005 | Daly et al. | |
| 2005/0217672 A1 * | 10/2005 | Bengtsson et al. | 128/204.18 |
| 2005/0217673 A1 | 10/2005 | Daly et al. | |
| 2006/0191531 A1 | 8/2006 | Mayer | |
| 2006/0237005 A1 | 10/2006 | Virr et al. | |
| 2007/0036662 A1 | 2/2007 | Pensola et al. | |
| 2007/0134085 A1 | 6/2007 | Daly et al. | |
| 2008/0162226 A1 | 7/2008 | Maresca et al. | |
| 2008/0304986 A1 | 12/2008 | Kenyon et al. | |
| 2009/0162226 A1 * | 6/2009 | Campbell | 417/423.14 |
| 2009/0229606 A1 | 9/2009 | Tang et al. | |
| 2010/0065051 A1 | 3/2010 | Potharaju et al. | |
| 2010/0229867 A1 | 9/2010 | Bertinetti et al. | |
| 2010/0307498 A1 | 12/2010 | Jones et al. | |
| 2010/0320755 A1 | 12/2010 | Williams et al. | |
| 2012/0266887 A1 | 10/2012 | Daly et al. | |

FOREIGN PATENT DOCUMENTS

| | | |
|---|---|---|
| DE | 275 612 C | 6/1914 |
| DE | 30 05 094 | 8/1981 |
| DE | 3623162 A1 | 7/1986 |
| DE | 3823242 A1 | 2/1990 |
| DE | 9014848.7 | 3/1991 |
| DE | 4138098 C2 | 11/1991 |
| DE | 41 11 138 A1 | 10/1992 |
| DE | 4244493 A1 | 7/1993 |
| DE | 93 17 450 | 6/1994 |
| DE | 3789221 T2 | 8/1994 |
| DE | 9409231.1 U1 | 12/1994 |
| DE | 19630466 | 2/1998 |
| DE | 29817685 U1 | 10/1998 |
| DE | 29909611 U1 | 10/1999 |
| DE | 199 36 499 A1 | 2/2001 |
| DE | 10016005 A1 | 12/2001 |
| DE | 102005007773 A1 | 9/2005 |
| EP | 0 290 062 A2 | 11/1988 |
| EP | 0 376 584 A2 | 7/1990 |
| EP | 0 589 429 A1 | 3/1994 |
| EP | 0 589 429 B1 | 3/1994 |
| EP | 0 893 750 | 1/1999 |
| EP | 1023912 A2 | 8/2000 |
| EP | 1 055 431 A2 | 11/2000 |
| EP | 1 087 322 A2 | 3/2001 |
| EP | 1318307 | 6/2003 |
| EP | 1 374 938 A1 | 1/2004 |
| FR | 2 323 436 | 4/1977 |
| FR | 2 714 985 | 7/1995 |
| GB | 1556492 A | 11/1979 |
| GB | 2177006 A | 1/1987 |
| JP | 38-15973 | 8/1938 |
| JP | 40-35414 | 12/1940 |
| JP | 53-104402 U | 8/1978 |
| JP | 64-80799 A | 3/1989 |
| JP | 3-47500 A | 2/1991 |
| JP | 3-253794 A | 11/1991 |
| JP | 0 471 089 A1 | 2/1992 |
| JP | 4-159500 A | 6/1992 |
| JP | 4-353299 A | 12/1992 |
| JP | 5-89887 U | 12/1993 |
| JP | 7-145795 A | 6/1995 |
| JP | 7-275362 A | 10/1995 |
| JP | 8-93691 A | 4/1996 |
| JP | 11-398 A | 1/1999 |
| JP | 11-148119 A | 6/1999 |
| JP | 2000-337670 A | 12/2000 |
| JP | 2001-160102 A | 6/2001 |
| JP | 2002-106495 A | 4/2002 |
| JP | 2002-206498 A | 7/2002 |
| JP | 2002-253672 | 9/2002 |
| JP | 2002-306601 | 10/2002 |
| JP | 2002-537006 A | 11/2002 |
| WO | WO 93/05451 A1 | 3/1993 |
| WO | WO 98/31937 A | 7/1998 |
| WO | WO 98/33433 | 8/1998 |
| WO | WO 98/57691 A1 | 12/1998 |

(56) References Cited

FOREIGN PATENT DOCUMENTS

| WO | WO 99/13932 | 3/1999 |
|---|---|---|
| WO | WO 99/22794 | 5/1999 |
| WO | WO 99/22794 A1 | 5/1999 |
| WO | WO 99/64747 | 12/1999 |
| WO | 00/21602 A1 | 4/2000 |
| WO | WO 00/27457 A1 | 5/2000 |
| WO | WO 00/42324 A | 7/2000 |
| WO | WO 01/32069 A2 | 5/2001 |
| WO | WO 01/73653 A1 | 10/2001 |
| WO | WO 02/02169 A1 | 1/2002 |
| WO | 02/066106 A1 | 8/2002 |
| WO | WO 03/040567 A1 | 5/2003 |
| WO | 2007/019625 | 2/2007 |
| WO | WO 2007/019628 A1 | 2/2007 |
| WO | 2007/048205 | 5/2007 |
| WO | 2007/048206 | 5/2007 |
| WO | 2007/134405 | 11/2007 |
| WO | WO 2009/059359 A1 | 5/2009 |
| WO | WO 2009/156921 A1 | 12/2009 |
| WO | WO 2010/092496 | 8/2010 |

OTHER PUBLICATIONS

Petition Exhibit 1004 in IPR2014-01363, Declaration of Steve Bordewick, Aug. 22, 2014, 90 pages.
Petition for *Inter Parties* Review of U.S. Pat. No. Re. 44,453 Under To 35 U.S.C. §§ 311 ET SEQ. and 37 C.F.R. §42.100 ET SEQ, *Apex Medical Corp.*, Petitioner v. *ResMed Limited*, Patent Owner, Case No. IPR2014-00551, Mar. 27, 2014, 38 pages.
Apex Medical Corporation, Petition Exhibit 1002 in IPR 2014-00551, "ResMed's First Amended Complaint for Patent Infringement—Jury Trial Demanded", Case No. SACV-13-00498 CJC (RNBx), USDC, Central District of California, Southern Division, 18 pages.
Petition Exhibit 1006 in IPR2014-00551, Patent Owner Amendment mailed Mar. 27, 2009, in U.S. Appl. No. 11/181,807, 10 pages.
Petition Exhibit 1007 in IPR2014-00551, Declaration of Joseph Dyro in Support of *Inter Partes* Review of U.S. Pat. No. Re. 44,453, executed Mar. 26, 2014, 15 pages.
Petition for *Inter Partes* Review of U.S. Pat. No. Re. 44,453 Under to 35 U.S.C. §§ 311-319 and 37 C.F.R. U.S.C. §42.100 et seq., *BMC Medical Co. Ltd.*, Petitioner v. *ResMed Limited*, Patent Owner, Case No. IPR2014-01196, Jul. 23, 2014, 62 pages.
Petition Exhibit 1003 in IPR2014-01196, REMStar® Heated Humidifier Manual, Mar. 15, 2001, 8 pages.
Petition Exhibit 1004 in IPR2014-01196, Declaration of Steve Bordewick, Jul. 22, 2014, 59 pages.
Petition Exhibit 1006 in IPR2014-01196, Patent Owner ResMed Limited's Preliminary Response filed Jul. 10, 2014, in IPR2014-00551, 41 pages.
Petition Exhibit 1007 in IPR2014-01196, ITC Investigation No. 337-TA-890,: Order No. 7: Initial Determination Granting Complainants' Motion to Amend Complaint and Notice of Investigation and Granting Respondents' Motion to Terminate the Investigation with Respect to U.S. Pat. No. 7,614,398, served Feb. 4, 2014, 8 pages.
Petition Exhibit 1009 in IPR2014-01196, Case No. SACV 13-00498: Order Granting Defendants' Motion to Stay Litigation Pending *Inter Partes* Review, Oct. 4, 2013, 3 pages.
Petition Exhibit 1010 in IPR2014-01196: Patent Prosecution History of Reissue U.S. Appl. No. 13/944,960, filed Jul. 18, 2013, 228 pages.
Petition Exhibit 1011 in IPR2014-01196: Patent Prosecution History of U.S. Pat. No. 7,614,398, 174 pages.
Petition Exhibit No. 1012 in IPR2014-01196: Patent Prosecution History of U.S. Pat. No. Re. 44,453, 2157 pages.
Petition Exhibit No. 1013 in IPR2014-01196: Proof of Service of 3B Medical, Inc. in Civil Action No. 13-cv-1246-MMA-WMC, 5 pages.
Petition Exhibit No. 1014 in IPR2014-01196: Australian Application No. PR 3117, filed Feb. 16, 2001, 17 pages.
Petition Exhibit No. 1015 in IPR2014-01196: ITC Investigation No. 337-TA-890: Order No. 8: Construing Terms of the Asserted Patents, served Jan. 17, 2014, 51 pages.
Petition Exhibit No. 1016 in IPR2014-01196: ITC Investigation No. 337-TA-890: Order No. 14: Denying Respondents' Motion for Summary Determination of Invalidity of U.S. Pat. No. Re. 44,453, served Mar. 26, 2014, 19 pages.
Petition Exhibit No. 1020 in IPR2014-01196: Australian Application No. PR 7288, filed Aug. 27, 2001, 23 pages.
Petition Exhibit No. 1022 in IPR2014-01196: ITC Investigation No. 337-TA-890: Notice of Commission Determination Not to Review an Initial Determination Granting the Complainants' Motion to Amend the Complaint and Notice of Investigation to Substitute U.S. Pat. No. Re. 44,453 for U.S. Pat. No. 7,614,398 and Granting Respondents' Motion to Terminate the Investigation with Respect to U.S. Pat. No. 7,614,398, Issued: Feb. 10, 2014, 3 pages.
Patent Owner Exhibit No. 2002 in IPR2014-00551, U.S. Pat. No. Re. 44,453 Patent Application Data Sheet, Initial May 4, 2011, 5 pages.
Patent Owner Exhibit No. 2003 in IPR2014-00551, Decision of the Patent Trial and Appeal Board Denying Institution of *Inter Partes* Review of U.S. Pat. No. 7,614,398, entered Feb. 20, 2014, 5 pages.
Fisher & Paykel Healthcare "SleepStyle™ 200 CPAP Series" Specification Sheet, 1998, 4 pages.
J. H. Emerson Co., Cough Assist, "Non-Invasive Removal of Bronchial Secretions," 2 pages.
Madaus Schwarzer Medizintechnik, "New Approaches in Diagnosis and Therapy—Moritz biLevel User Manual", May 1994, 38 pages.
German Patient Manual for Hoffrichter/Sandmann CPAP Respirator—Perfect CPAP Therapy, 30 pages plus Translation Verification Certificate, Mar. 1998.
Breas Medical AB "iSleep® 20" Brochure, Dec. 2007, 2 pages.
Fisher & Paykel Healthcare "SleepStyle™ 600 CPAP Series" Specification Sheet, 2005, 4 pages.
Fisher & Paykel Healthcare Two Easy Steps to Comfort, Humidification and Nasal CPAP Therapy, Aug. 1995, 4 pages.
Hoffrichter GmbH "VECTOR therapy in perfection" Brochure, 2002, 2 pages.
MAP Medizin-Technologie GmbH "minni Max nCPAP®, The respiratory therapy device with•out an integrated humidifier", Dec. 2003, 17 pages.
MAP Medizintechnik fuer Arzt und Patient "max II nCPAP moritz II biLevel—The gentle therapy for sleep-related breathing disorders" Brochure, 2000, 4 pages.
Respironics "System One Heated Humidifier User Manual", May 2009, 20 pages.
De Vilbiss® Healthcare, "DeVilbiss IntelliPAP® Standard CPAP System," Nov. 2007, 2 pages.
Photos of HumidAire™, 11 pages.
Photos of tray system available before the critical date, with sample flow generator and humidifier, 5 pages.
Microfilm of Japanese Utility-Model Application No. S54-003858 (Japanese Utility-Model Application Publication No. S55-104925).
MAP Medizintechnik, "minni Max nCPAP®" brochure, 12 pages, Mar. 2005.
MAP Medizintechnik, "Moritz II biLEVEL®—The gentle therapy for sleep-related breathing disorders" brochure, 6 pages, Jan. 2001.
Photos of MAP Humidifier and Tub, 2 pages and cover sheet, undated.
ResMed "Sullivan® HumidAire® User's Instructions", 8 pages, 1998.
MAP Medizin-Technologie GmbH, Moritz®S/Moritz®ST—Sailing toward therapeutic success . . . , Jul. 2004, 4 pages.
Hoffrichter "Vector CPAP—Therapy With Technical Mastery", 4 pages, Oct. 1998.
Patent Owner Exhibit No. 2001 in IPR2014-00551, Applicant Transmittal to USPTO re Completion of National Phase Filing of the PCT Application for the Mayer Reference, Aug. 6, 2002, 4 pages.

(56) References Cited

OTHER PUBLICATIONS

ITC Action related to Certain Sleep-Disordered Breathing Treatment Systems and Components Thereof, Inv. No. 337-TA-, CBI 13-185, filed on Mar. 28, 2013, 57 pages.
ResMed's First Amended Complaint for Patent Infringement, filed in the United States District Court Central District of California Southern Division, filed on Apr. 8, 2013, 342 pages.
"Complaint for Patent Infringement—Jury Trial Demanded" as filed in the United States District Court, Southern District of California, Case No. '13CV1246 MMAWMC, dated May 31, 2013, 18 pages.
"Motion to Amend the Complaint and Notice of Investigation" as filed in the United States International Trade Commission, Investigation No. 337-TA-879, dated May 31, 2013, 18 pages.
Final Notice of Reasons for Rejection delivered Sep. 24, 2008 in Japanese Appln. No. 2002-565664, with English translation (6 pages).
Notification of the First Office Action mailed Jul. 22, 2005 in Chinese Appln. No. 02804936.5, with English translation (8 pages).
Extended European Search Report mailed Apr. 28, 2011 in European Appln. No. 10189422.8 (5 pages).
International Search Report mailed Mar. 21, 2002 in International Appln. No. PCT/AU02/00155 (2 pages).
International Preliminary Examination Report completed Oct. 4, 2002 in International Appln. No. PCT/AU02/00155 (3 pages).
Office Action dated Jan. 22, 2008 in Japanese Patent Appln. No. 2002-565665 (w/English translation) (12 pages).
Examination Report mailed Oct. 10, 2003 in New Zealand Appln. No. 527088 (2 pages).
Supplementary European Search Report mailed Sep. 15, 2009 in European Appln. No. 02700014.0, (3 pages).
Fischer & Paykel, "Two Easy Steps to Comfort", 4 pages, Aug. 1995.
Appeal Decision mailed Oct. 18, 2011 in Japanese Appln. No. 2006-515536 (Appeal No. 2011-1175), with English Translation (17 pages).
Communication mailed Apr. 27, 2012 in European Application No. 04 736 483.1 (5 pages).
Notice of Reasons for Rejection mailed Jul. 31, 2012 in Japanese Application No. 2011-007878, with English Translation (9 pages).
J.H. Emerson Co., Cough Assist, "Non-Invasive Removal of Bronchial Secretions", Date unknown but prior to the date of this application, 2 pgs.
International Search Report for PCT/AU2004/000771, mailed Aug. 23, 2004, 6 pages.
Examiner's First Report Mailed May 30, 2011 in Australian Application No. 2011202113 (2 pages).
Supplementary European Search Report Mailed Jun. 17, 2011 in European Application No. 0473648.1 (3 pages).
Notice of Reasons for Rejection mailed Apr. 23, 2013 in Japanese Application No. 2012-039850, with English Translation (7 pages).
Requisition by the Examiner mailed Apr. 26, 2013 in Canadian Application No. 2,528,384.
Communication mailed Jul. 1, 2010 in European Appln. No. 02 700 014.0 (5 pages).
Extended European Search Report mailed May 4, 2012 in European Appln. No. 12159042.6 (5 pages).
Madaus Schwarzer Medizintechnik, "New Approaches in Diagnosis and Therapy—Max nCPAP User Manual", Mar. 1994, 38 pages.
Patent Owner Exhibit No. 2005 in IPR2014-00551, U.S. National Stage Worksheet of USPTO re National Phase Requirements Completion for the Mayer Reference, 1 page.
Patent Owner Exhibit No. 2010 in IPR2014-00551, Deposition Transcript of Dr. Joseph F. Dyro in Connection with *Inter Partes* Review Proceedings IPR2013-00511, IPR2013-00512, IPR2013-00514, IPR2013-00515, and IPR2013-00516, Apr. 21, 2014, 46 pages.
Patent Owner Exhibit No. 2011 in IPR2014-00551, Patent Owner ResMed Limited's Preliminary Response to Apex Medical Corp.'s Petition for *Inter Partes* Review of U.S. Pat. No. 7,614,398, Case No. IPR2013-00513, Nov. 22, 2013, 15 pages.
Notification of Acceptance of Request for Invalidation and English Translation for corresponding Chinese Patent No. 02804936.5, issued Mar. 20, 2014, 188 pages.
Petition Exhibit 1008 in IPR2014-01196, Case No. 13-cv-1246-CAB (WMC), Order on Motion to Stay, Motion to Dismiss, and Related Discovery Request, Oct. 15, 2013, 3 pages.
Notice of Reasons for Rejection mailed Apr. 23, 2013 in Japanese Application No. 2011-007878, with English Translation (9 pages).
ResMed, "The Sullivan® HumidAire™", 1997, 1 page.
Fisher & Paykel Healthcare "SleepStyle™ 200 CPAP Series" Specification Sheet, 2005, 4 pages.
Fisher & Paykel Healthcare, "HC200 Series Nasal CPAP Blower & Heated Humidifier User's Manual", 1998, 17 pages.

* cited by examiner

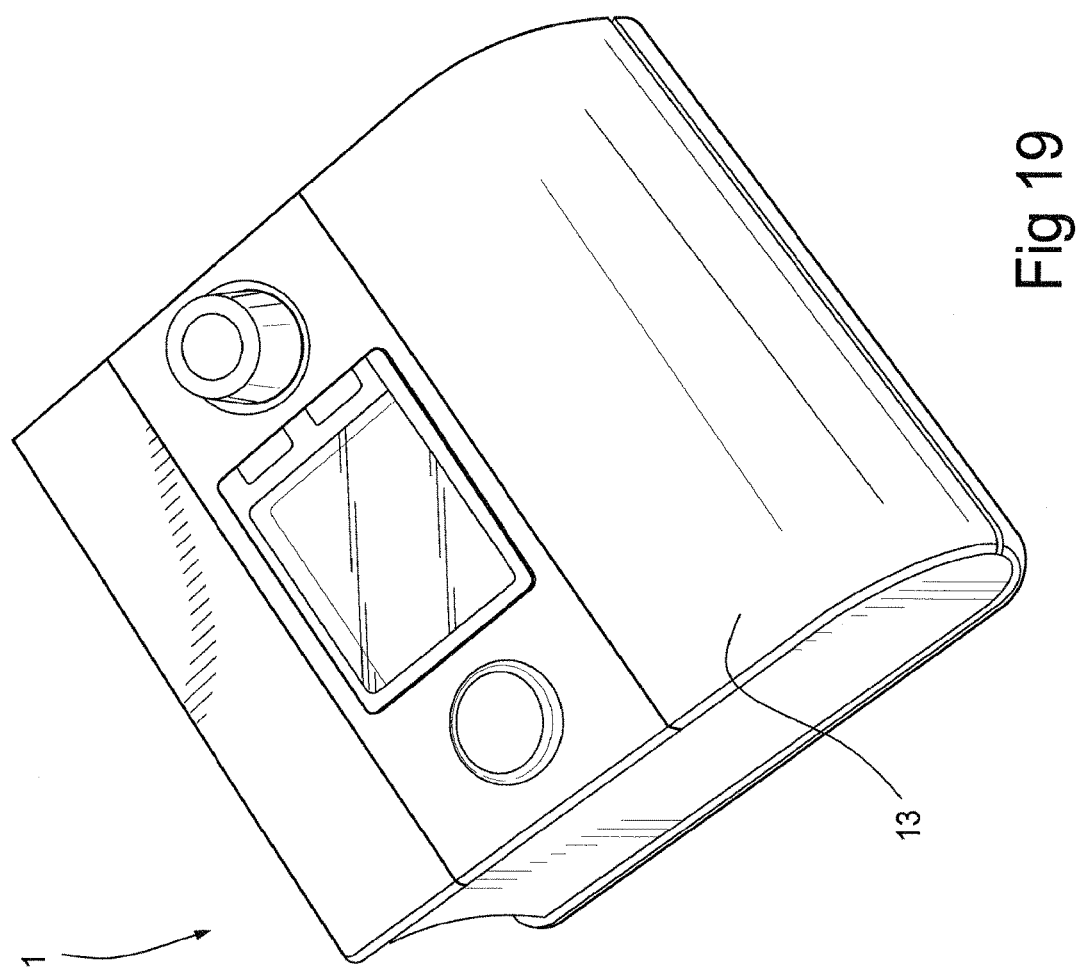

FLOW GENERATOR CHASSIS ASSEMBLY WITH SUSPENSION SEAL

CROSS REFERENCE TO RELATED APPLICATIONS

This application is a continuation of U.S. application Ser. No. 12/794,206, now allowed, filed Jun. 4, 2010, which claims the benefit of U.S. Application 61/184,124, filed Jun. 4, 2009, the entire contents of which are incorporated herein by reference.

FIELD OF THE INVENTION

The present technology relates to a flow generator for generating a flow of breathable gas to be delivered to a patient. In an embodiment, the flow generator may be used in a positive airway pressure (PAP) device used for the delivery of respiratory therapy to a patient. Examples of such therapies are Continuous Positive Airway Pressure (CPAP) treatment, Non-Invasive Positive Pressure Ventilation (NIPPY), Variable Positive Airway Pressure (VPAP), and Bi-Level Positive Airway Pressure. The therapy is used for treatment of various respiratory conditions including Sleep Disordered Breathing (SDB) and more particularly Obstructive Sleep Apnea (OSA). The present technology also relates to a seal for the flow generator. The present technology further relates to methods of assembling a flow generator.

BACKGROUND

Flow generators are used to generate a flow of breathable gas for treatment of various respiratory conditions. The flow generator may be configured to be connected to a patient interface, for example a mask, to deliver the flow of breathable gas to the patient's airways. The flow generator may also be configured to be connected to a humidifier configured to store a supply of water for humidifying the flow of breathable gas prior to delivery to the patient.

A blower is provided in the flow generator to generate the flow of breathable gas. A blower may comprise a motor comprising a rotating part including, for example, a shaft having an impeller(s) mounted thereon, and a non-rotating part. The operation of the motor may generate noise and vibration. As the therapy may be delivered to the patient during sleep, the generation of noise and vibration may reduce the effectiveness of the therapy.

The flow generator may also include electronics configured to control the operation of the motor of the blower to vary the pressure of the flow of breathable gas that is generated by the blower. The electronics may be damaged by the flow of breathable gas generated by the blower, for example by debris drawn into the flow generator.

A flow sensor may be provided to measure the volume of the flow of breathable gas generated by the blower. Gaps in the flow generator chassis assembly may allow portions of the flow of breathable gas to bypass the flow sensor, thus providing an inaccurate measure of the flow.

BRIEF SUMMARY

According to one aspect, a flow generator chassis assembly is provided with a seal that is configured to mount the blower.

According to another aspect, the seal is configured to align the motor of the blower.

According to still another aspect, the seal is configured as a suspension for the blower.

According to a further aspect, the seal is configured to seal between high and low pressure sides of the flow generator chassis assembly.

According to yet another aspect, the seal is configured to seal an inlet air flow path and/or an outlet air flow path of the flow generator chassis assembly.

According to another aspect, the seal is configured to seal a portion of the flow generator chassis assembly from which a wire of the blower motor extends out of the chassis assembly.

According to a further aspect, the seal is configured to seal between acoustic chambers of the flow generator chassis assembly.

According to still another aspect, the seal is configured to seal an air flow path through the flow generator chassis assembly from electronics contained in the flow generator chassis assembly.

According to yet another aspect, the seal may be configured to include a flow sensor tube seal and a manifold connection to the flow sensor.

According to one sample embodiment of the technology, a seal is provided for a chassis assembly of a flow generator configured to provide a flow of breathable gas. The chassis assembly includes an upper chassis and a lower chassis. The seal comprises a blower receptacle sealing portion configured to seal a blower receptacle of the chassis assembly configured to receive a blower configured to generate the flow of breathable gas; a flow sensor sealing portion configured to seal a flow sensor provided in the chassis assembly and configured to measure the flow of breathable gas; a blower mount configured to receive a portion of the blower and mount the blower to the seal; and a blower mount suspension configured to connect the blower mount to the blower receptacle sealing portion, wherein in an assembled condition the seal and the chassis assembly define a flow path from an inlet of the chassis assembly to the blower receptacle of the chassis assembly to an outlet of the chassis assembly.

According to another sample embodiment, a flow generator for generating a flow of breathable gas comprises a chassis assembly comprising a lower chassis and an upper chassis, the lower chassis and the upper chassis defining a blower receptacle; a blower provided in the blower receptacle; and a seal according to at least the preceding paragraph.

According to still another sample embodiment, a method of assembling a flow generator, for example as described above, comprises mounting the blower to the blower mount of the seal; positioning the seal on the lower chassis; routing the wire of the blower through the grommet of the seal; and fastening the upper chassis and the lower chassis together.

According to yet another sample embodiment, a method of assembling a flow generator, for example as described above, comprises mounting the blower to the blower mount of the seal; aligning the seal on the upper chassis; positioning the lower chassis on the seal; and fastening the upper chassis and the lower chassis together.

According to a further sample embodiment, a flow generator for generating a pressurized flow of breathable gas comprises a chassis comprising a lower chassis and an upper chassis, the lower chassis and the upper chassis defining an enclosure; a blower provided in the enclosure and configured to generate a flow of breathable gas from air drawn through an inlet in the chassis and deliver the flow of breathable gas to an outlet in the chassis; and a blower mount between the lower chassis and the upper chassis that mounts the blower in the enclosure. The blower mount comprises a blower receptacle that receives a lower portion of the blower, a blower mount outlet configured to deliver the flow of breathable gas from the blower to the outlet in the chassis, and a seal in engagement with the upper chassis to provide a sealed air flow path from an inlet of a upper chassis blower receptacle to the blower mount outlet.

Other aspects, features, and advantages of the technology will become apparent from the following detailed description when taken in conjunction with the accompanying drawings, which are a part of this disclosure and which illustrate, by way of example, principles of the technology.

BRIEF DESCRIPTION OF THE DRAWINGS

The accompanying drawings facilitate an understanding of the various embodiments of this invention. In such drawings:

FIG. 19 is a perspective view of the flow generator including an outer casing.

DETAILED DESCRIPTION OF THE ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

Chassis

Figure 1:
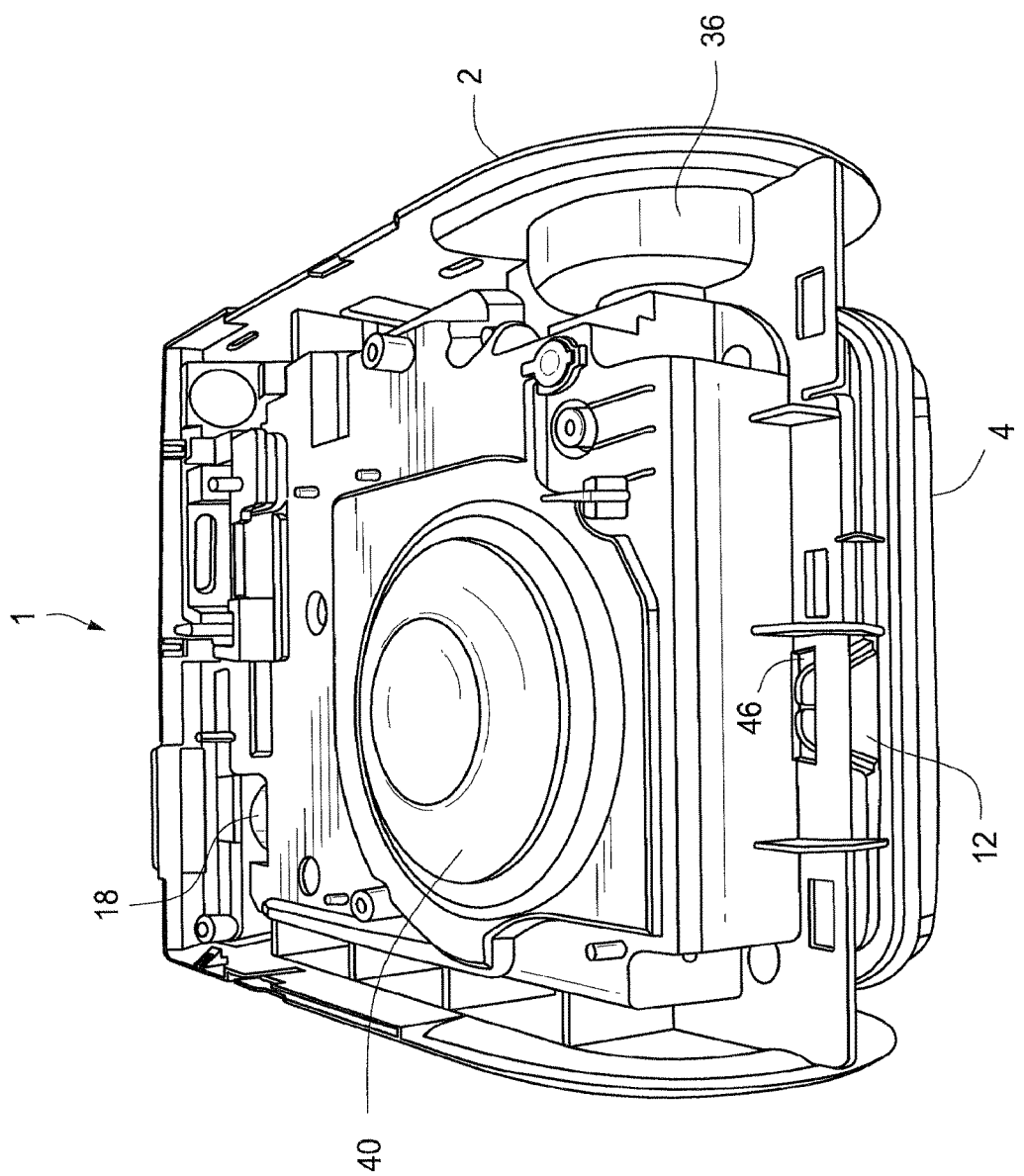
FIG. 1 is a top perspective view of a flow generator according to a sample embodiment.
Figure 2:
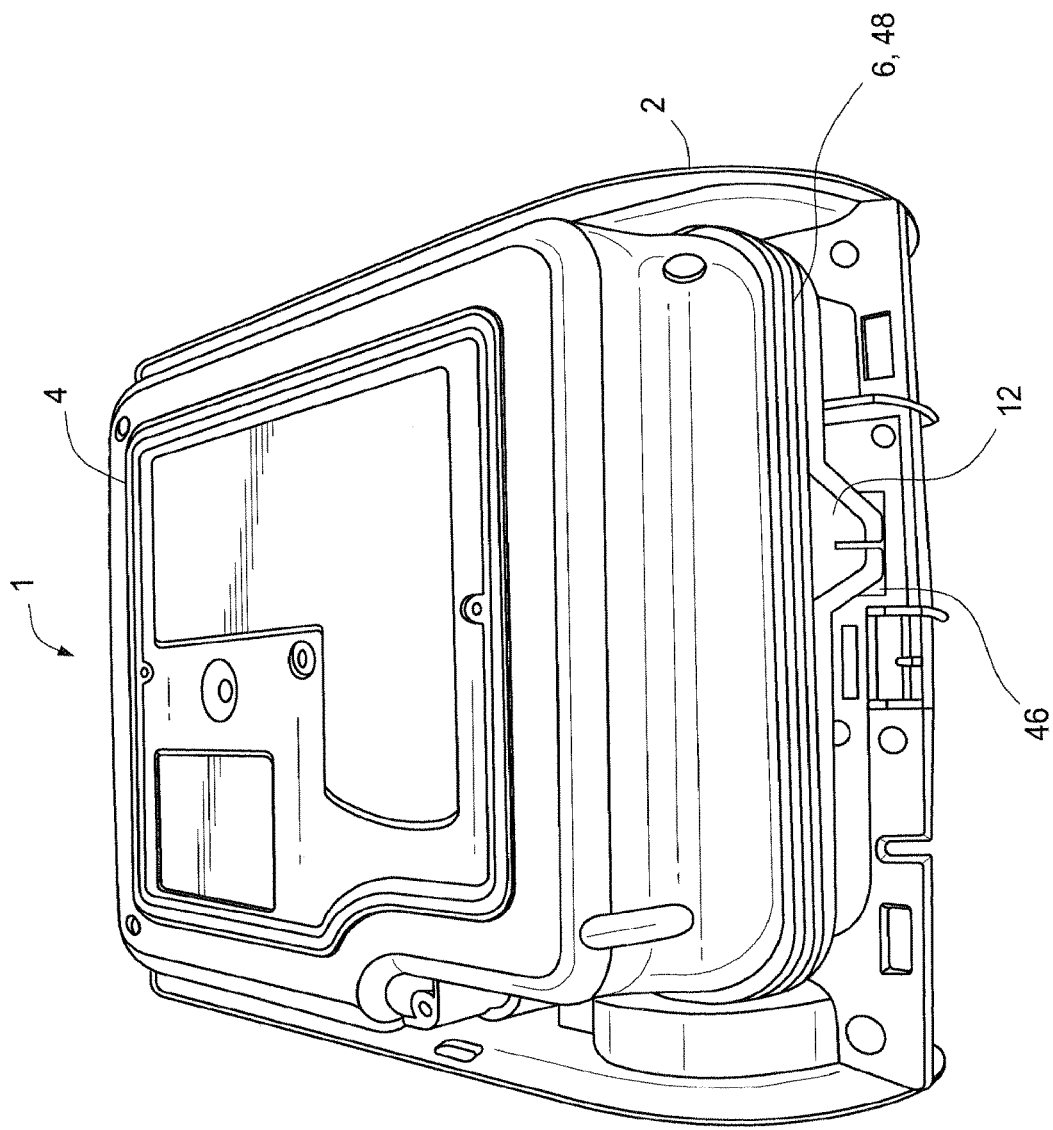
FIG. 2 is a bottom perspective of the flow generator of FIG. 1.
Figure 3:
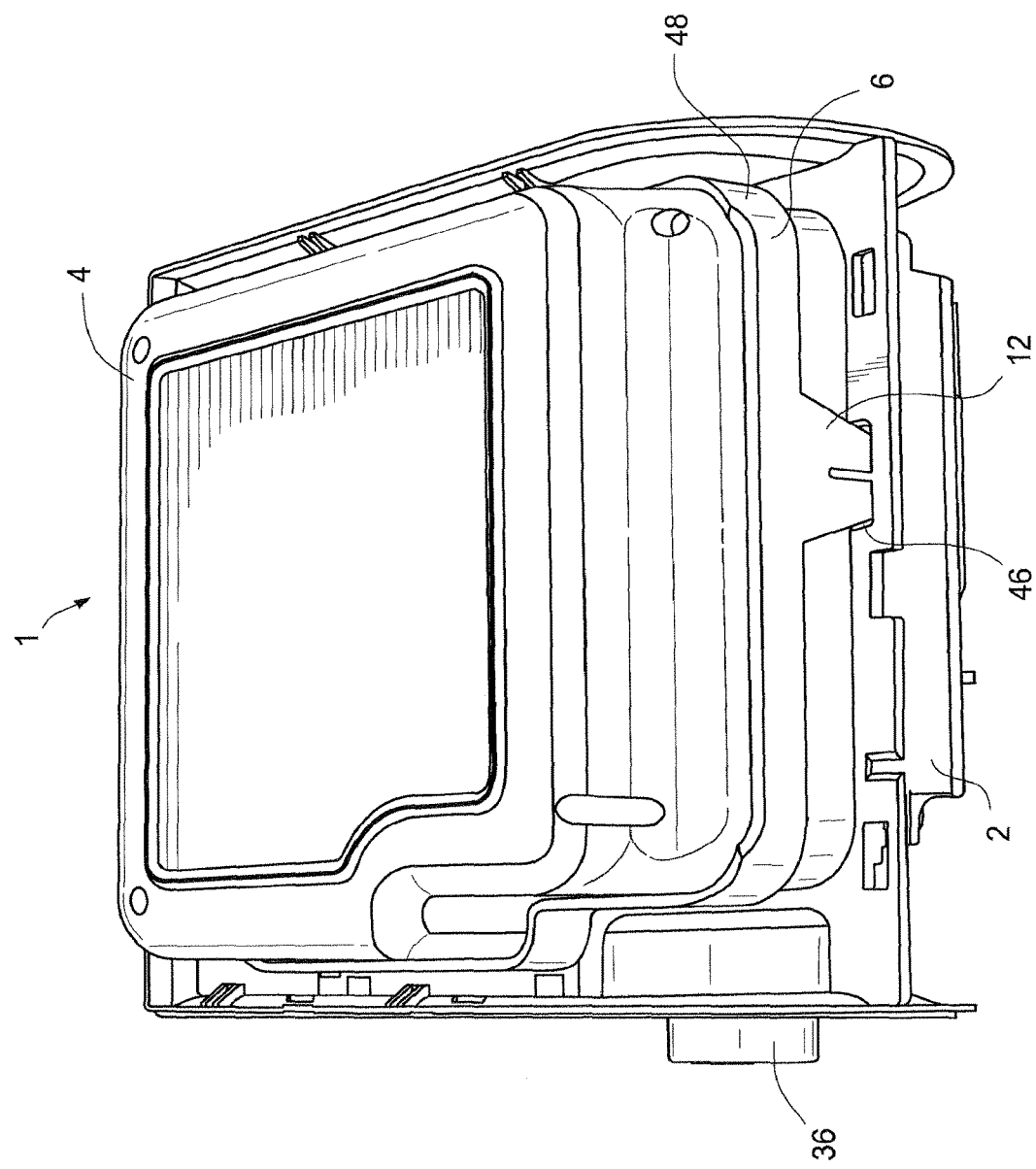
FIG. 3 is a bottom perspective of the flow generator of FIG. 1.
Figure 4:
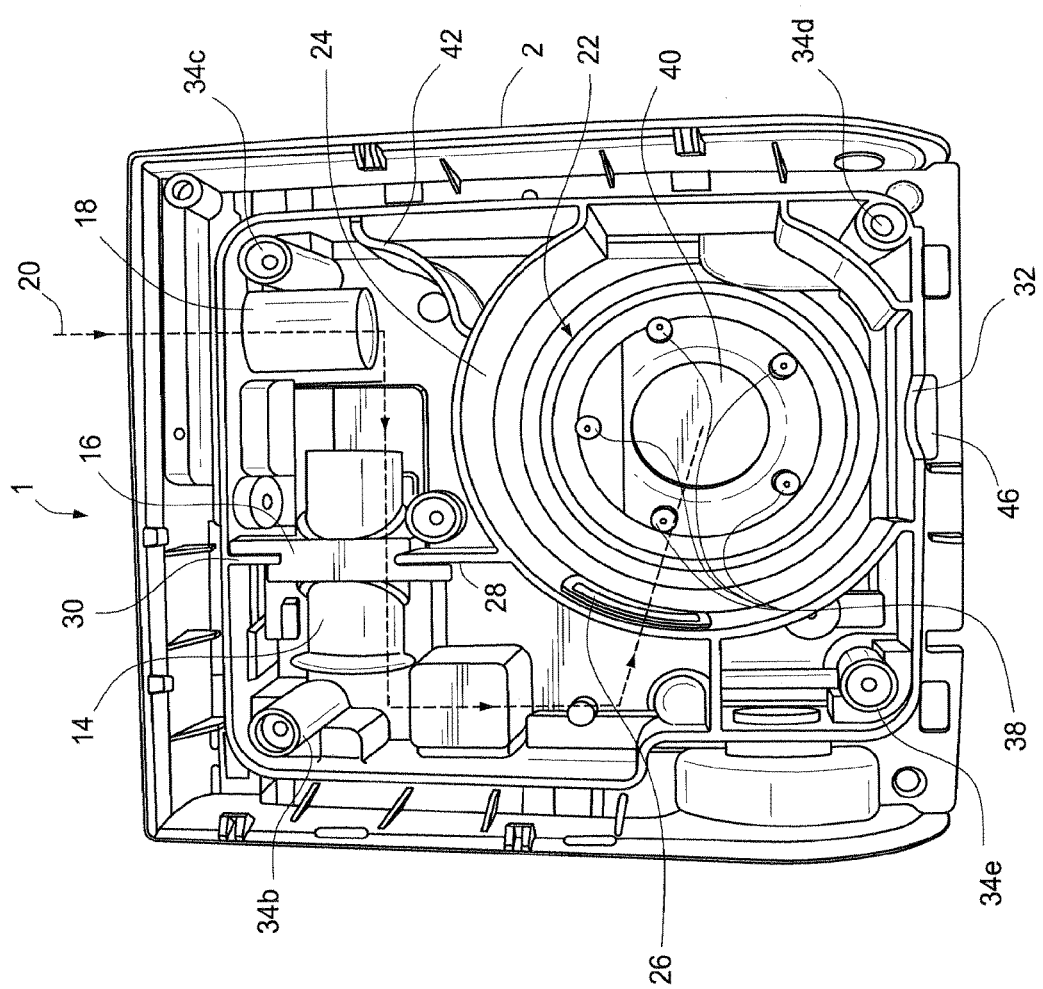
FIGS. 4-7 are perspective views of the upper chassis of the flow generator according to a sample embodiment.

Referring to FIG. 1, a chassis assembly of a flow generator 1 includes an upper chassis 2 and a lower chassis 4. The upper chassis 2 and the lower chassis 4 may be formed of, for example, plastic. The upper chassis 2 includes an air flow outlet 36 that is configured to be connected to a tube or conduit for delivery of a flow of breathable gas to a patient interface that is configured to engage the patient to deliver the flow of breathable gas. It should also be appreciated that the air flow outlet 36 is configured to be connected to the inlet of a humidifier configured to store a supply of water for humidifying the flow of breathable gas. Referring to FIG. 19, the flow generator 1 may comprise an outer casing 13 that covers and/or surrounds the chassis assembly.

The upper chassis 2 also includes an upper chassis receptacle top portion 40 that is configured to receive the top of a blower 10 (FIG. 13) described in more detail below. The blower is configured to generate the flow of breathable gas, e.g. in the range of about 2-30 cm $H_2O$, from air drawn through an air inlet 18 provided in the upper chassis 2.

A grommet 12 of a flow generator seal extends through a grommet slot 46 provided in the upper chassis 2.

Blower Mount

Referring to FIGS. 2, 3, 8 and 9, the blower mount, or flow generator seal, 6 is provided between the upper chassis 2 and the lower chassis 4. As discussed in more detail below, the flow generator seal 6 provides a sealed inlet air path for the flow generator 1. The sealed inlet air path directs the inlet air flow through an inlet filter and prevents the air flow from leaking through gaps in the case formed by the upper chassis 2 and the lower chassis 4. The inlet air flow thus does not flow over the electronics. The sealing of the air flow also reduces noise leakage through the gaps in the case. It should be appreciated, however, that the flow generator seal 6 may not include an inlet air path seal.

As shown in FIGS. 2, 3, 8, 9, 12-15 and 17, the flow generator seal 6 includes a flow generator seal skirt 48 having a T-shaped cross section that extends around the perimeter of the flow generator seal 6 and engages the upper chassis 2 and the lower chassis 4 to seal the junction between the upper chassis 2 and the lower chassis 4.

The seal 6 may be formed of a flexible material, for example silicone. The seal may also be formed so as to be elastically deformable, for example to stretch, to permit the seal to engage various portions of the flow generator chassis assembly and/or blower while in a deformed, e.g. stretched, condition. The seal may also be transparent or translucent. In other sample embodiments, the seal may also comprise a frame or support, e.g. a rigid support skeleton, that may be, for example, overmolded onto the flexible material (or the flexible material of the seal may be overmolded onto the frame or support), that provides additional locations for other components of the flow generator and/or aids in assembly of the flow generator.

Upper Chassis

Referring to FIGS. 4-7, the upper chassis 2 comprises the air inlet 18. An air inlet flow path 20 is established by the operation of a blower that is provided in an upper chassis blower receptacle 22 when the upper chassis 2, the flow generator seal 6, and the lower chassis 4 are assembled. The air inlet flow path 20 includes a flow sensor 14 that is supported in the upper chassis 2 between a pair of interior walls 28, 30. A flow sensor seal 16 is provided to prevent the inlet air flow path 20 from bypassing the flow sensor 14. It should be appreciated that the flow sensor seal 16 may be provided separately from the seal 6. It should also be appreciated that the flow sensor seal 16 may be integrally formed with the seal 6 and include the manifold connection to the flow sensor 14. It should be further appreciated that other sensors, e.g. pressure and/or thermistor, may be sealed, for example by integrally forming other sensor seals with the flow generator seal 6.

After passing through the flow sensor 14, the inlet air flow path 20 passes through a side wall air inlet 26 provided in the upper chassis blower receptacle side wall 24. The upper chassis blower receptacle 22 comprises a plurality of upper chassis bump stops 38 and a grommet notch 32 that is configured to receive the grommet 12 of the flow generator seal 6 that is configured to hold the electrical wire extending from the blower that is contained in the upper chassis blower receptacle 22. The upper chassis 2 also comprises a grommet slot 46 that the grommet 12 passes through.

A plurality of upper chassis fastener receptacles 34*a*-34*e* are provided in the upper chassis 2 and are configured to receive fasteners 88 (FIG. 18) that are configured to assemble the upper chassis 2, the flow generator seal 6 and the lower chassis 4 in to the flow generator 1.

Figure 5:
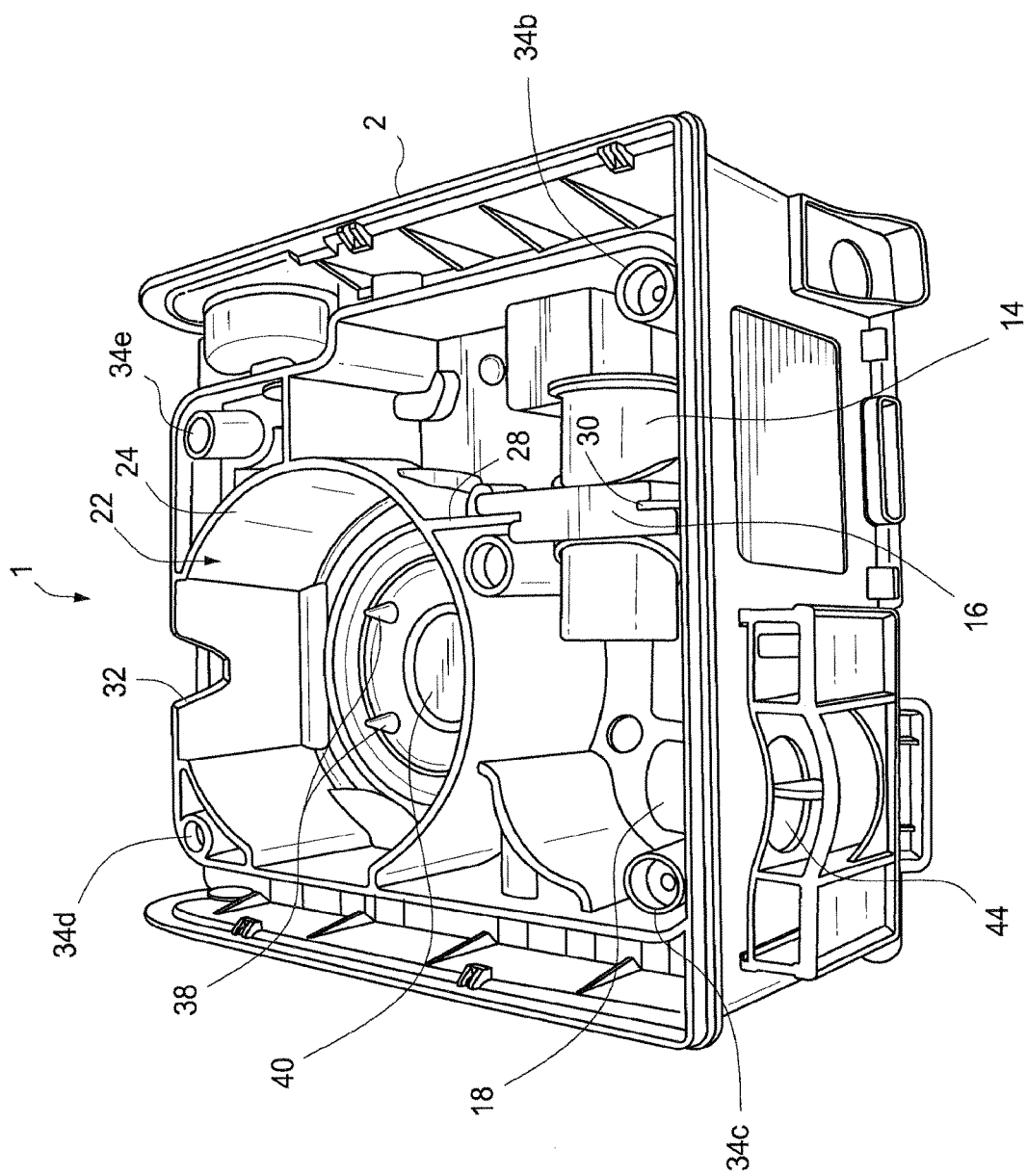
Figure 6:
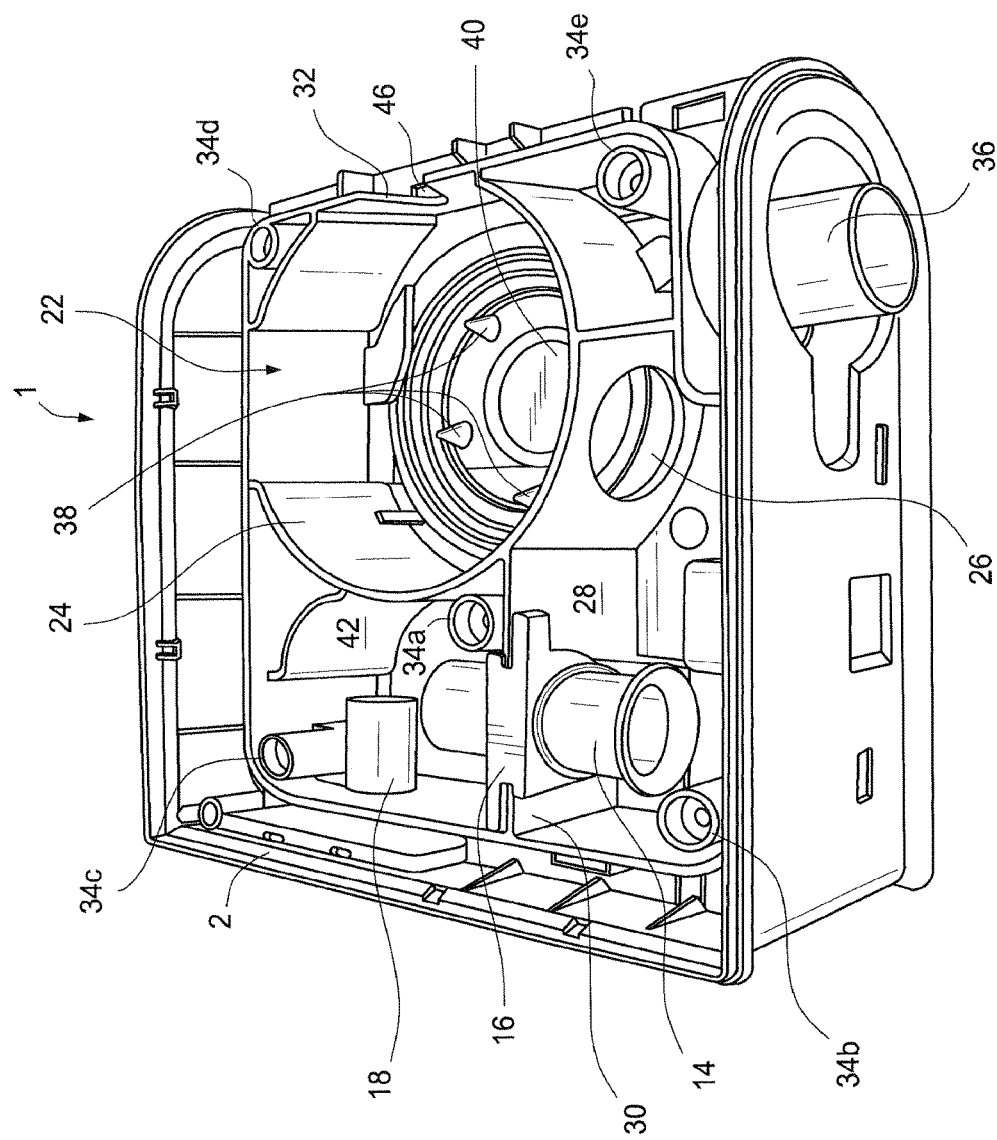
Figure 7:
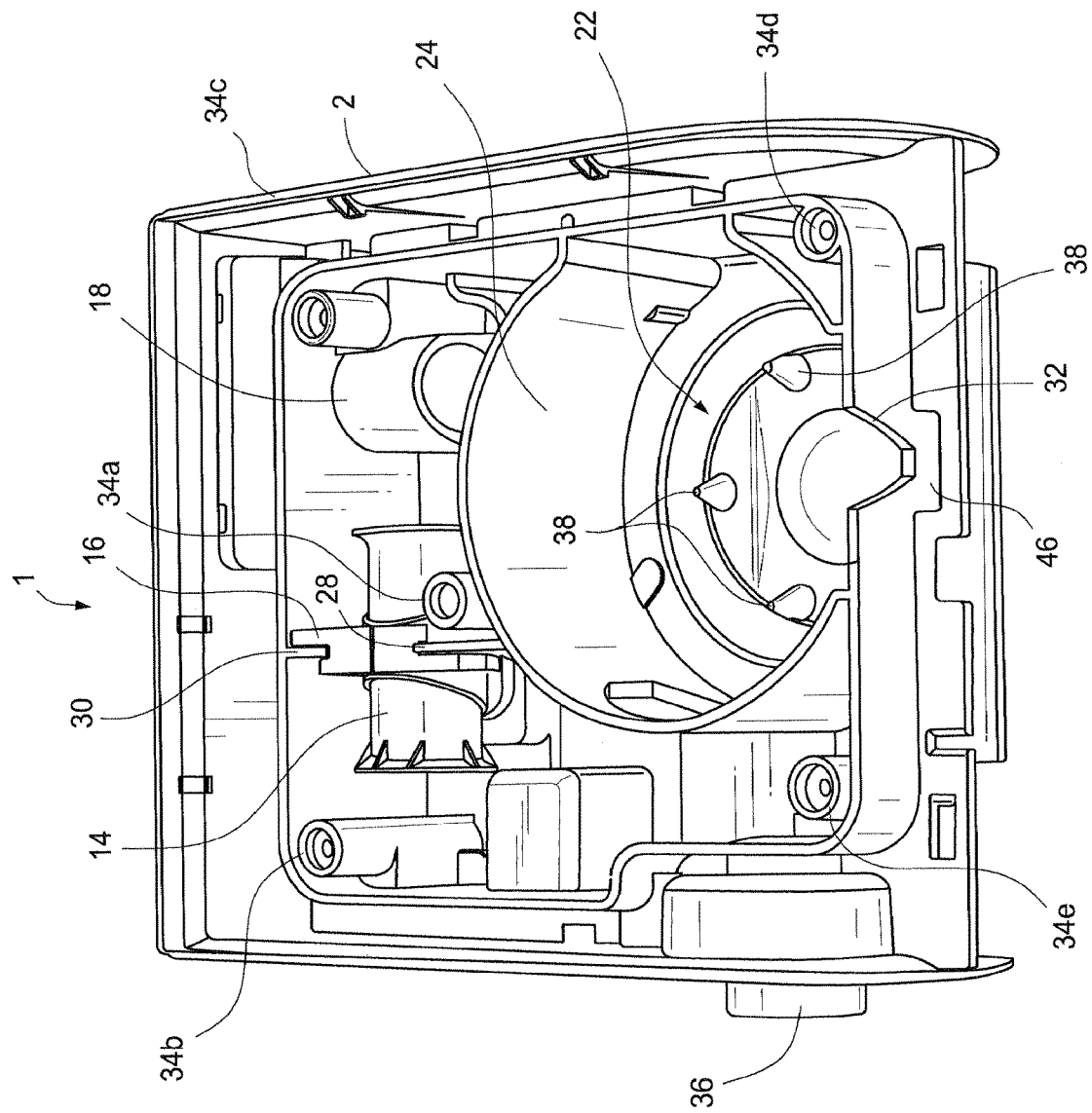

As shown in FIG. 5, the air inlet 18 of the upper chassis 2 includes an air inlet aperture 44 formed on a side wall of the upper chassis 2. It should be appreciated that an air inlet filter may be provided at the air inlet aperture 44 to filter air drawn in to the flow generator 1 by the blower.

Figure 8:
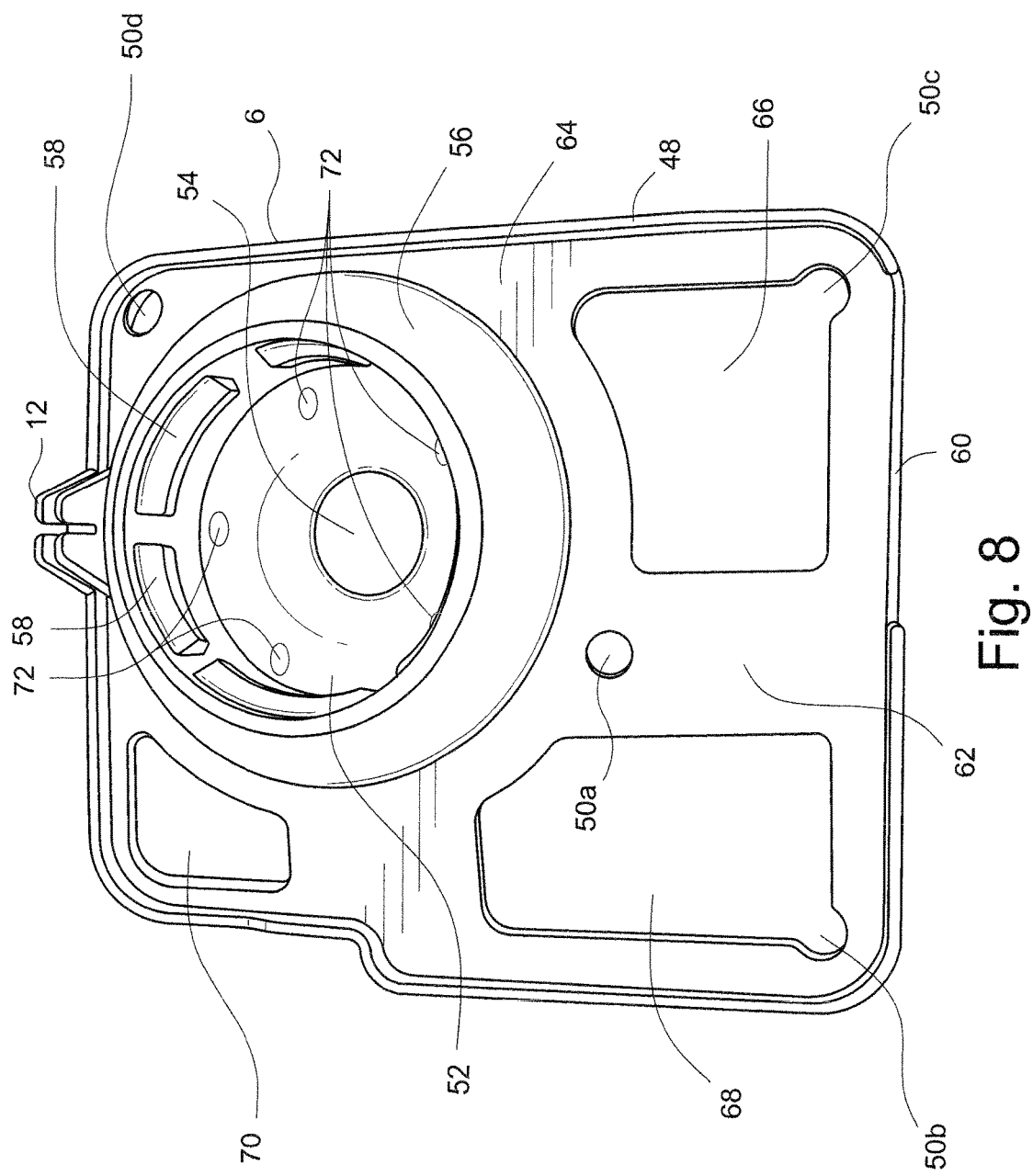
FIG. 8 is a top perspective view of a flow generator seal according to a sample embodiment.
Figure 9:
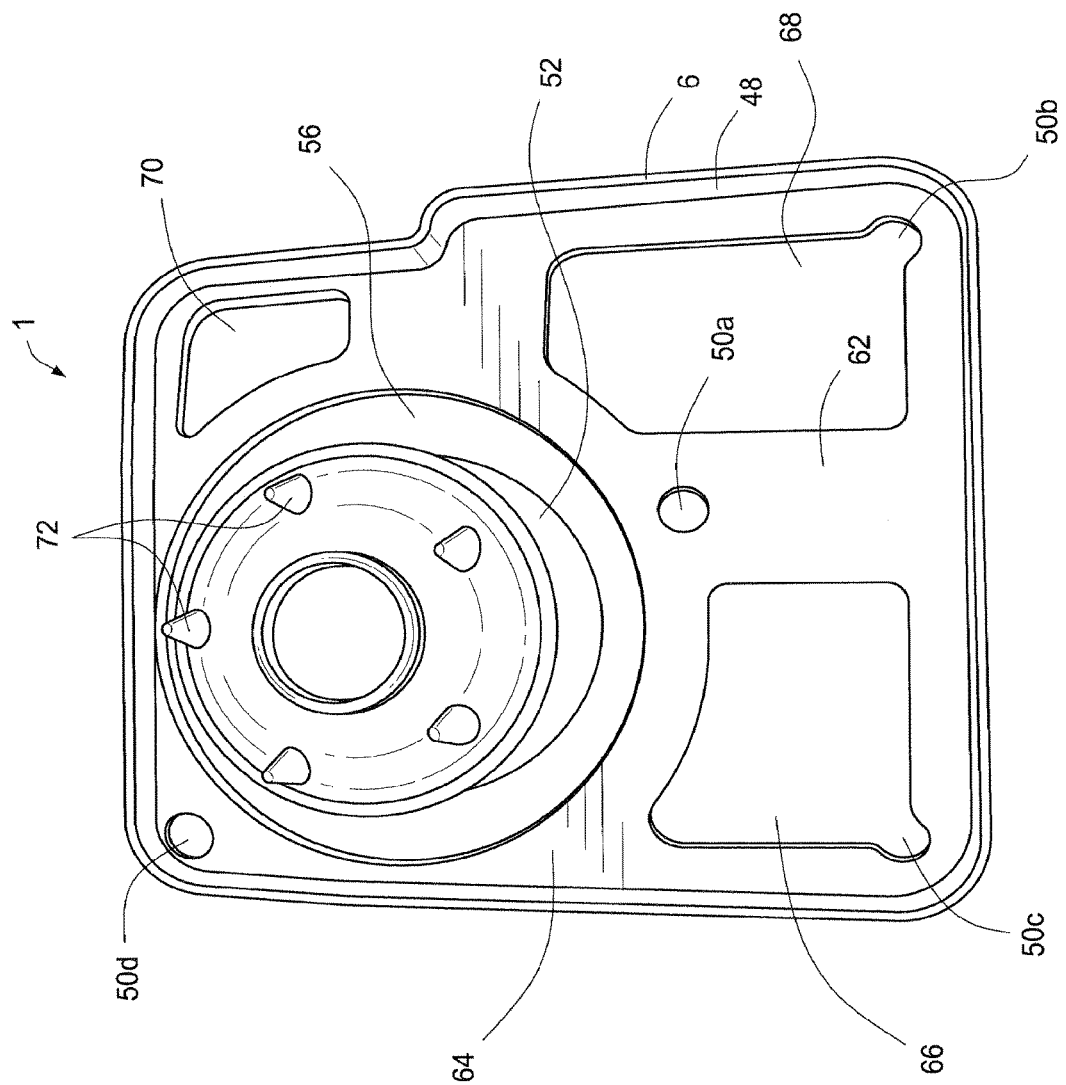
FIG. 9 is a bottom perspective view of the flow generator seal of FIG. 8.

Referring to FIGS. 8 and 9, the flow generator seal 6 comprises the T-shaped skirt 48 that extends around the perimeter of the flow generator seal 6. As shown in FIG. 8, a flow generator seal inlet portion 60 is provided on the flow generator seal 6. The T-shaped skirt 48 does not extend above the perimeter of the flow generator seal 6 in this region of the flow generator seal inlet portion 60 which is configured to be aligned with the air inlet aperture 44 and the air inlet 18 of the upper chassis 2. The skirt is L-shaped in cross section in the region of the seal inlet portion 60 and extends below the perimeter of the flow generator seal 6 and engages the perimeter of the lower chassis 4.

On the side opposite of the flow generator seal inlet portion 60, the flow generator seal 6 comprises the wire grommet 12 that is configured to hold the wire extending from the motor of the blower. A flow sensor seal portion 62 extends between the side including the inlet portion 60 and a blower receptacle and mount suspension 56 provided on the flow generator seal 6. The wire grommet 12 may be located at other positions on the seal 6, however locating the wire grommet 12 adjacent to the blower receptable and mount suspension 56 minimizes the length of the wires.

The blower receptacle and mount suspension 56 has a frusto-conical shape and supports a blower receptacle and mount 52 that is configured to receive a portion of the blower. As shown in FIG. 9, the blower receptacle and mount 52 comprises a plurality of flow generator seal bump stops 72 that are configured to prevent the blower bumping into the lower chassis 4.

The blower receptacle and mount 52 also comprises a plurality of blower receptacle and mount ribs 58 spaced around a periphery of the receptacle and mount 52 that are configured to engage the blower. The blower receptacle mount 52 also comprises a blower receptacle and mount outlet 54 through which the flow of breathable gas generated by the blower passes through to the outlet 36 of the flow generator 1.

The flow generator seal 6 includes a plurality of flow generator seal fastener openings 50*a*-50*d* that correspond to the upper chassis fastener receptacles 34*a*-34*d*. The fastener openings 50*a*-50*d* allow the fasteners to pass through to permit the upper chassis 2, the flow generator seal 6, and a lower chassis 4 to be assembled in to the flow generator 1.

A blower receptacle seal portion 64 extends circumferentially around the blower receptacle and mount suspension 56 and is configured to provide a seal around the blower received in the blower receptacle and mount 52. An air inlet seal opening 66 is provided adjacent to the blower receptacle seal portion 64 and the air inlet flow path 20 passes the air inlet seal opening in to the side wall air inlet 26 of the side wall 24 of the blower receptacle 22 of the upper chassis 2.

The air inlet seal opening 66 is provided adjacent to the blower receptacle seal portion 64 in the region of the air inlet 18 of the upper chassis 2 to permit the inlet air flow path to enter the flow generator 1 through the air inlet 18. An air flow outlet seal opening 70 is provided adjacent to the blower receptacle seal portion 64 so that the flow of breathable gas produced by the blower can pass to the outlet 36 of the flow generator 1.

Lower Chassis

Figure 10:
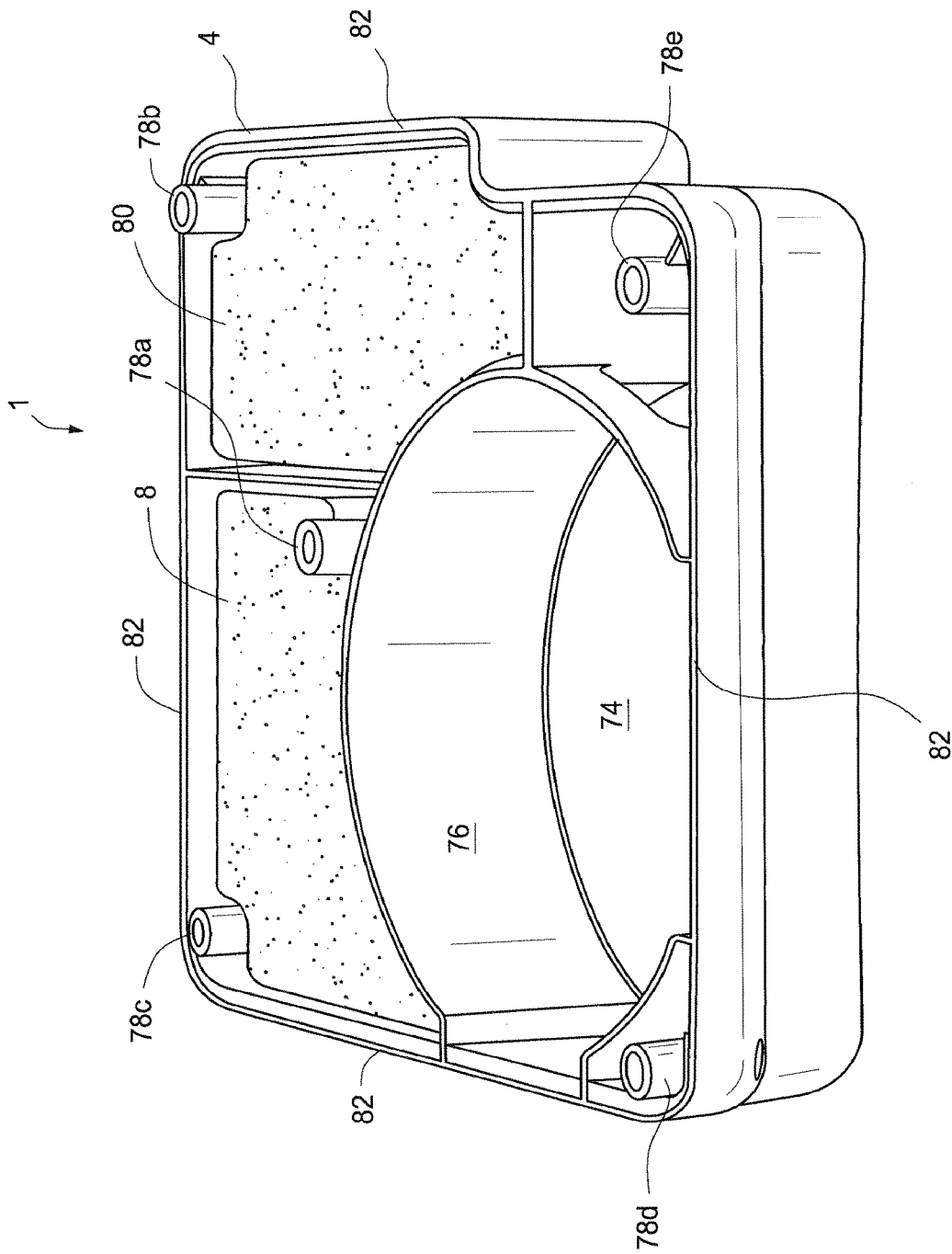
FIG. 10 is a perspective view of a lower chassis of the flow generator according to a sample embodiment.

Referring to FIG. 10, the lower chassis 4 includes a lower chassis blower receptacle 74 that comprises a lower chassis blower receptacle side wall 76 that is configured to receive a portion of the blower. A plurality of lower chassis fastener receptacles 78*a*-78*e* are provided that correspond to the upper chassis fastener receptacle openings 34*a*-34*e* and the flow generator seal fastener openings 50*a*-50*d*.

Referring still to FIG. 10, the compartment of the lower chassis 4 that corresponds to the blower inlet seal opening 68 of the flow generator seal 6 may comprise a foam 80. The compartment of the lower chassis 4 that corresponds to the air inlet seal opening 66 of the flow generator seal 6 may comprise a foam 8.

Figure 11:
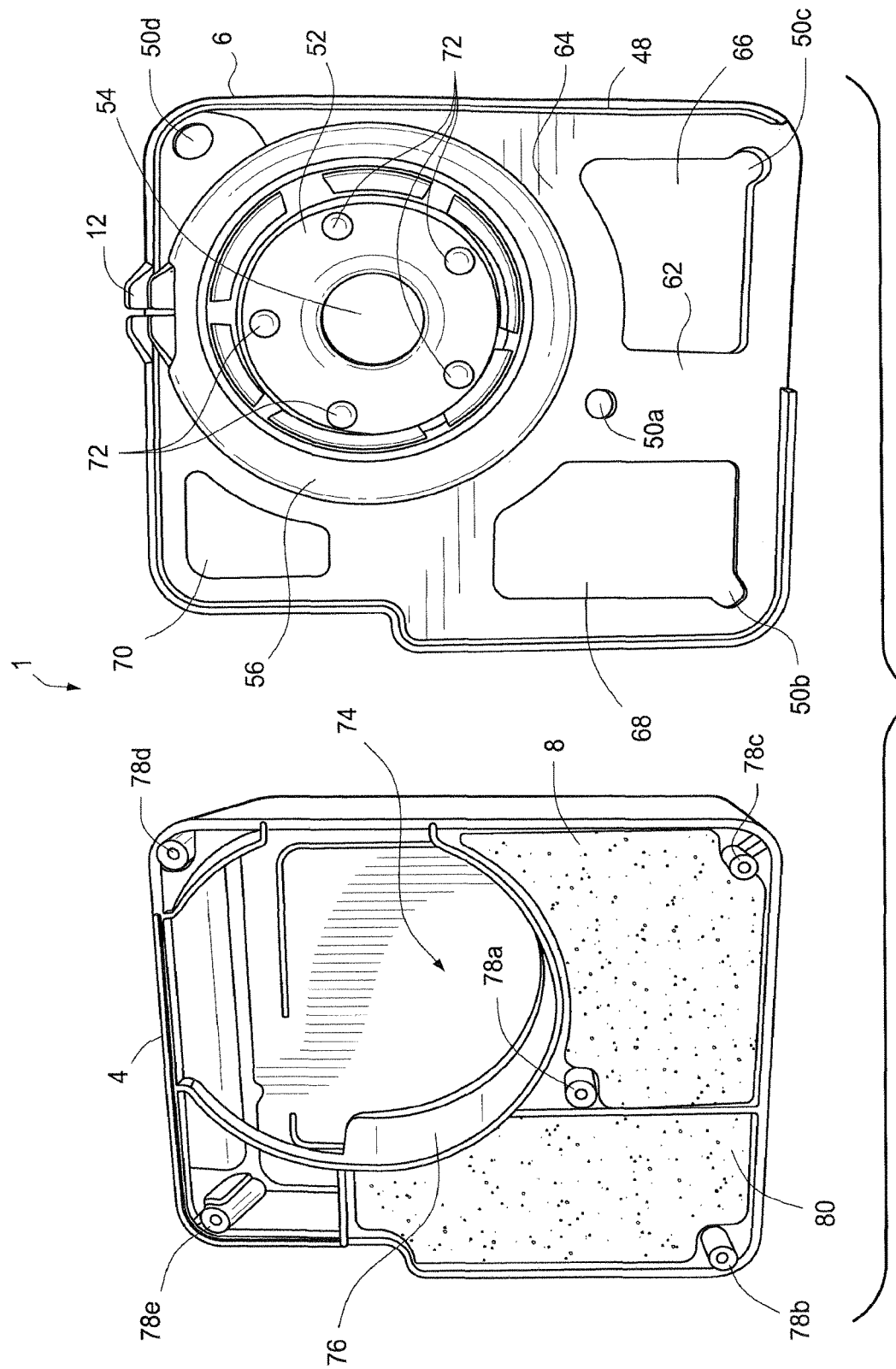
FIG. 11 is a perspective view of the lower chassis and the flow generator seal prior to assembly.
Figure 12:
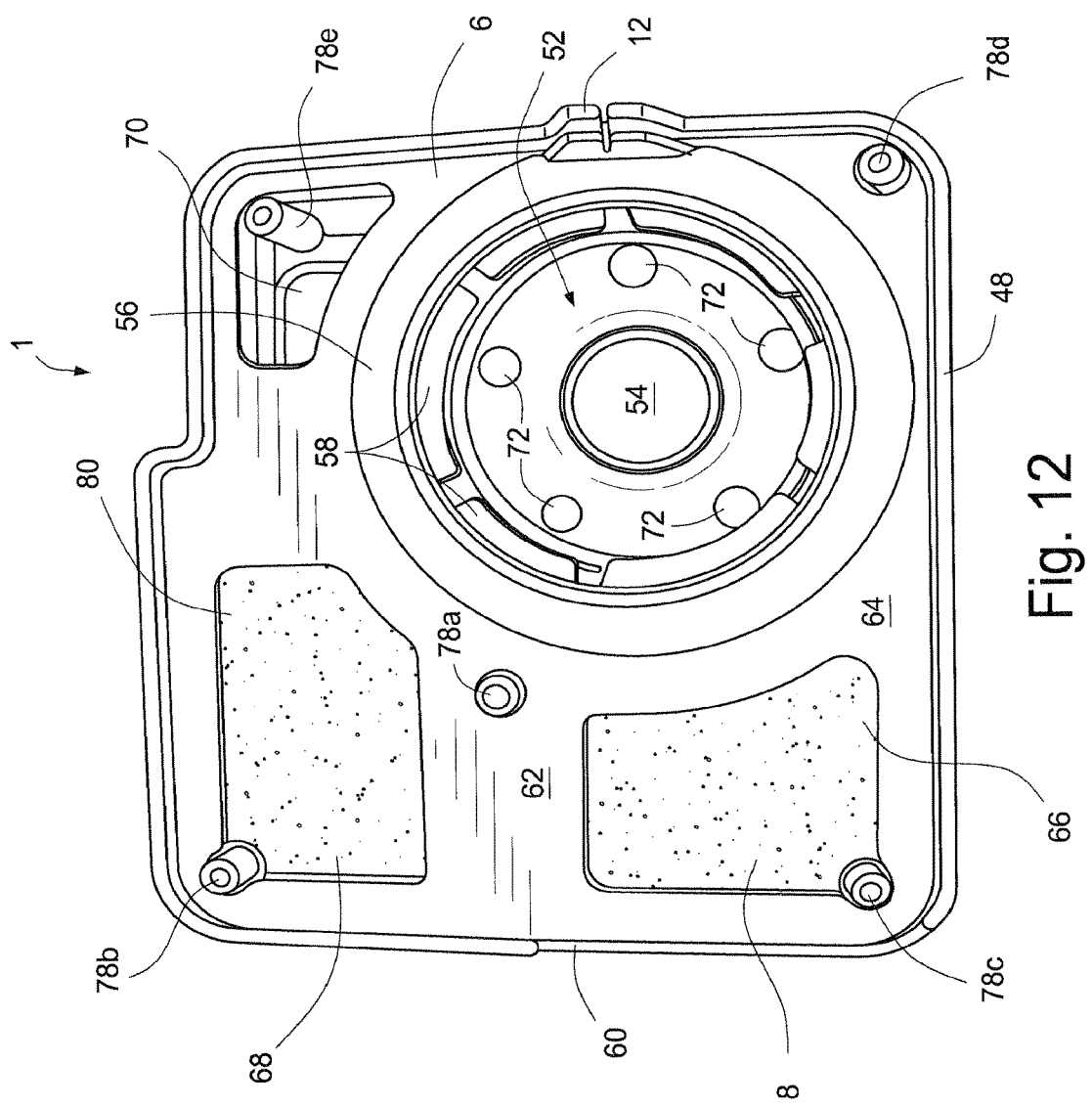
FIG. 12 is a perspective view of the lower chassis and flow generator seal after assembly.

Referring to FIG. 11, the flow generator seal 6 has a perimeter 82 that corresponds in shape to the perimeter of the lower chassis 4. As shown in FIG. 12, in the assembled condition, the flow generator seal 6 is provided around the lower chassis 4 so that the T-shaped skirt 48 of the flow generator seal 6 sealingly engages the perimeter of the lower chassis 4. The lower chassis fastener receptacles 78*a*-78*d* extend through the flow generator seal openings 50*a*-50*d*. The foam 8 is exposed through the air inlet seal opening 66 and the foam 80 is exposed through the blower inlet seal opening 68.

Blower and Blower Mount

Figure 13:
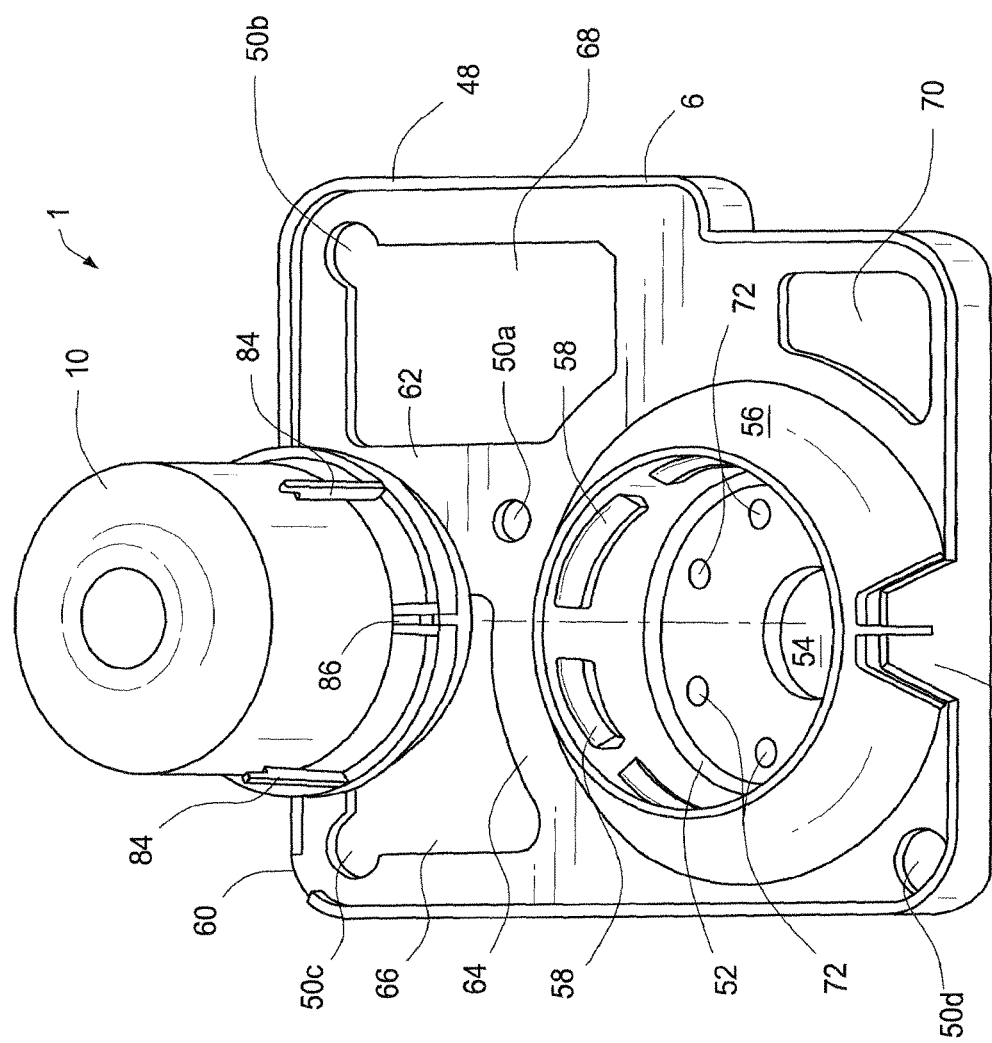
FIG. 13 is an exploded perspective view of the flow generator seal and a blower of the flow generator according to a sample embodiment.
Figure 14:
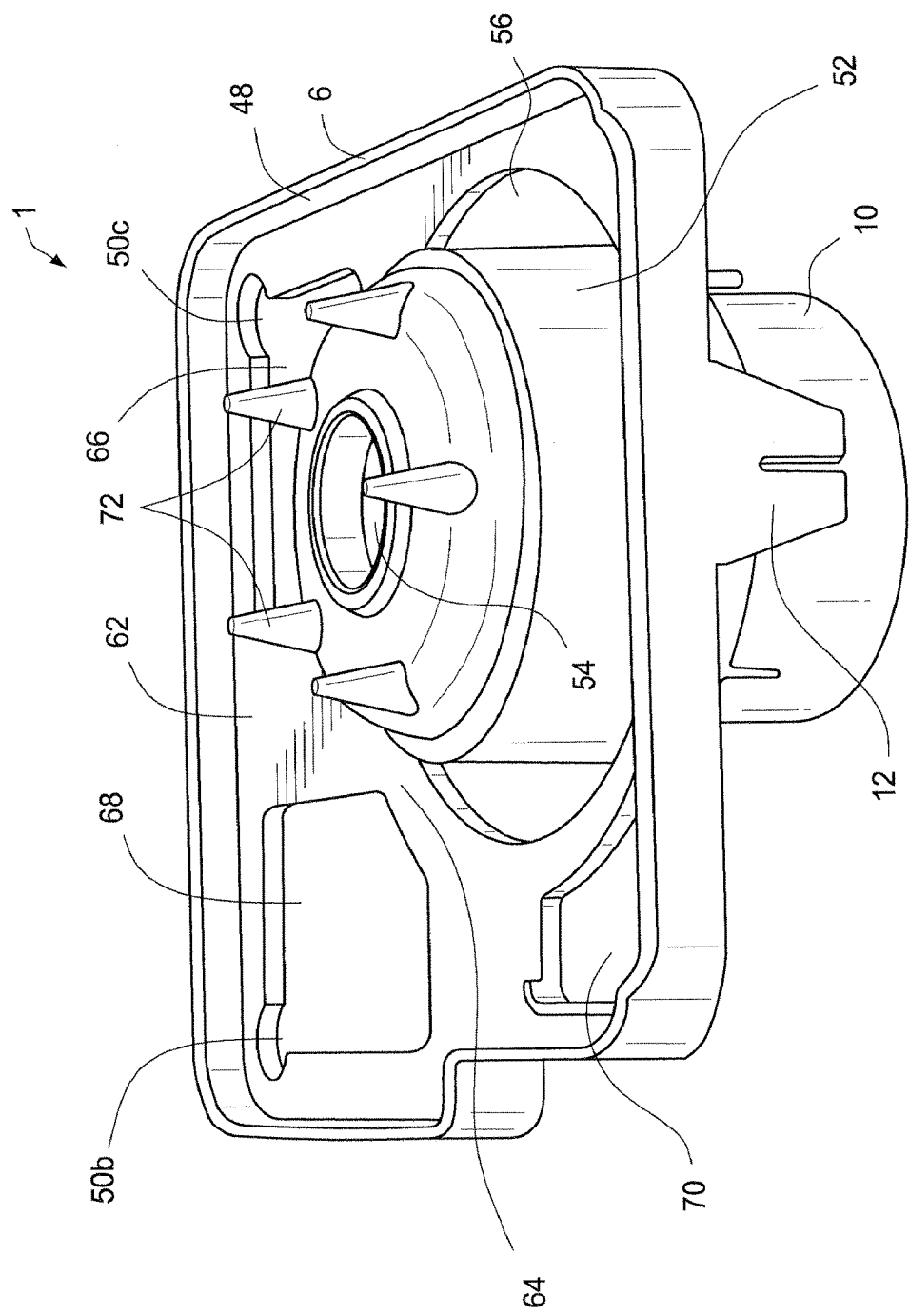
FIG. 14 is a perspective view of the blower and flow generator seal of FIG. 13 in an assembled condition.

Referring to FIGS. 13 and 14, the blower 10 is configured to be received in the blower receptacle mount 52 of the flow generator seal 6. The blower 10 may be as disclosed in, for example, in WO 2007/048205 A1, WO 2007/048206 A1, WO 2007/134405 A1, or U.S. Patent Application Publication 2008/0304986 A1, the entire contents of each being incorporated herein by reference. The motor and blower may be configured to provide a flow of breathable gas at a constant pressure, a variable pressure, or a bi-level pressure.

The outer periphery of the blower 10 may comprise blower alignment tabs 84 that are configured to be received between adjacent blower receptacle and mount ribs 58. The blower 10 also comprises a blower wire guide 86 that guides the wire from the motor of the blower 10 which is configured to be aligned with the wire grommet 12 of the flow generator seal 6, as shown in FIG. 15.

In use, when the blower 10 is running, the upper chassis 2 is the low pressure side and the lower chassis 4 is the high pressure side of the seal 6. The pressurized chamber causes the blower 10 to lift off the lower chassis 4 such that the blower 10 is suspended by the seal 6. The flow generator seal bump stops 72 and the upper chassis bump stops 38 are configured to prevent the blower 10 from bumping into the lower chassis 4 and the upper chassis 2, respectively.

Flow Generator Assembly

Figure 15:
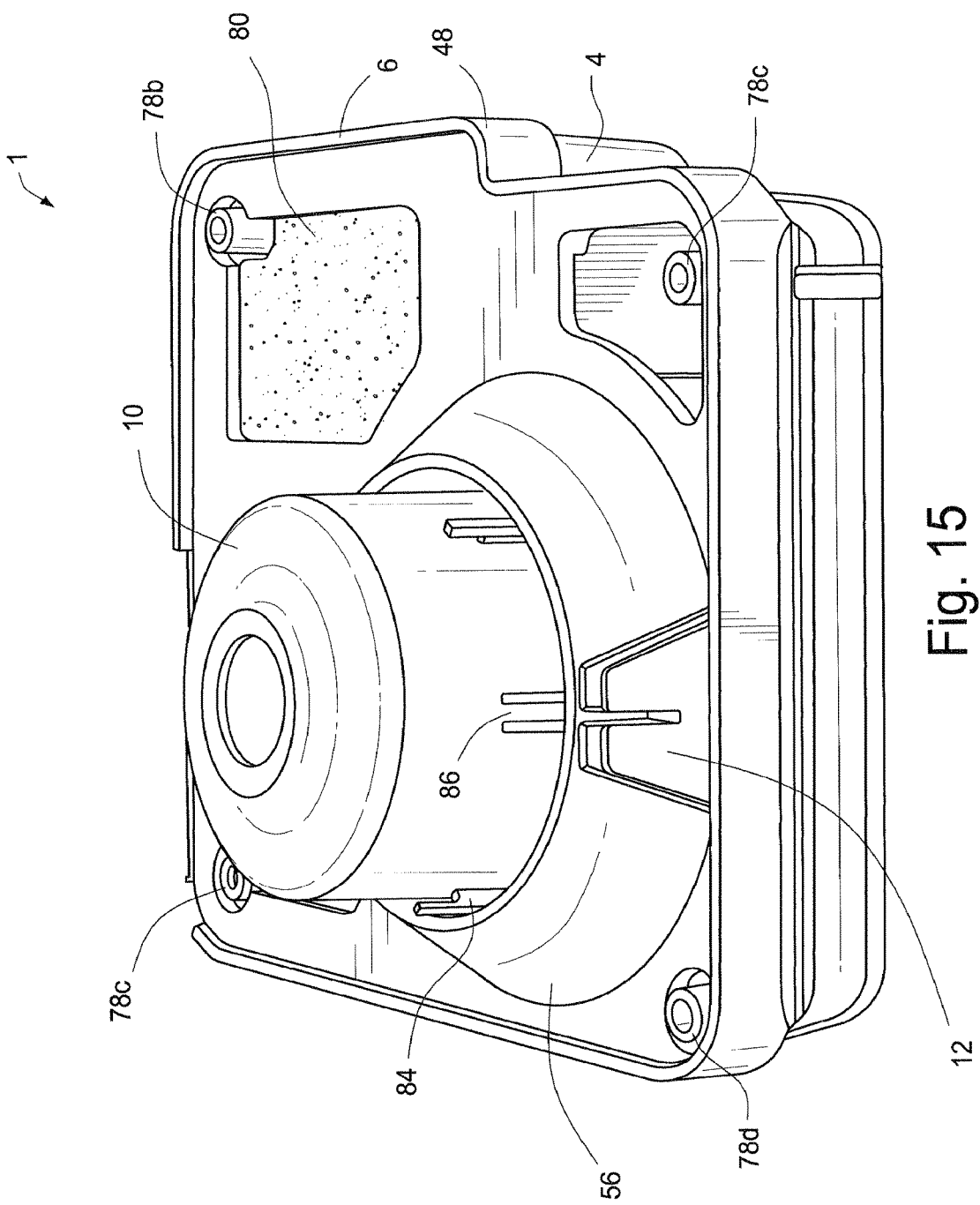
FIG. 15 is a perspective view of the flow generator seal and blower in an assembled condition.
Figure 16:
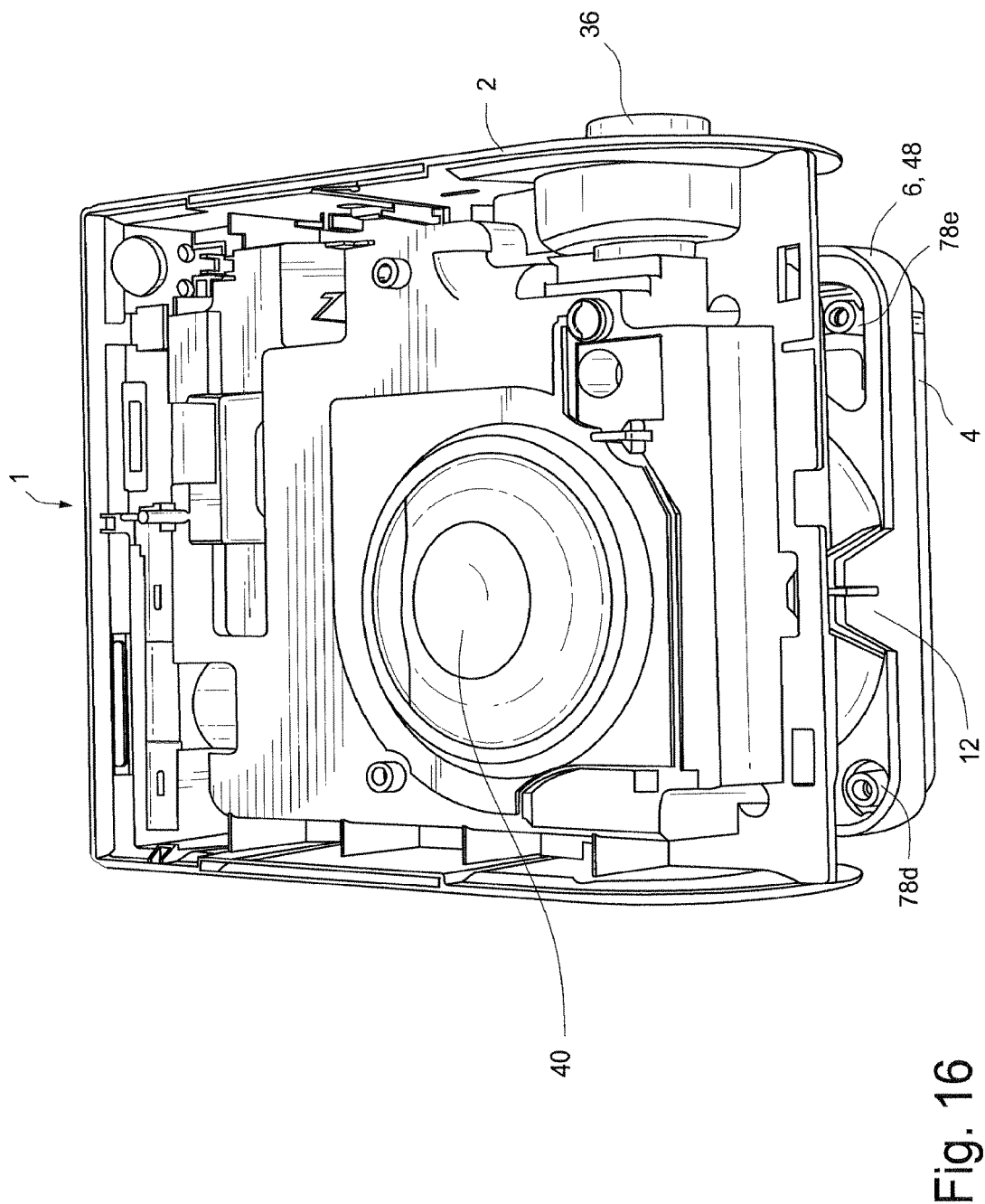
FIG. 16 is a perspective of the flow generator assembly prior to assembly according to one sample embodiment.

As shown in FIGS. 13-16, according to one sample embodiment of an assembly method, the flow generator seal 6 may be assembled with the blower 10, as shown in FIGS. 13 and 14. The flow generator seal and blower assembly 6, 10 may then be assembled on to the lower chassis 4 as shown in FIG. 15. Then, as shown in FIG. 16, the upper chassis 2 may be assembled to the lower chassis 4 and the flow generator seal and blower assembly 6, 10 shown in FIG. 15. The upper chassis 2 is assembled to the lower chassis 4 so that the blower 10 is received in the upper chassis receptacle top portion 40.

Figure 17:
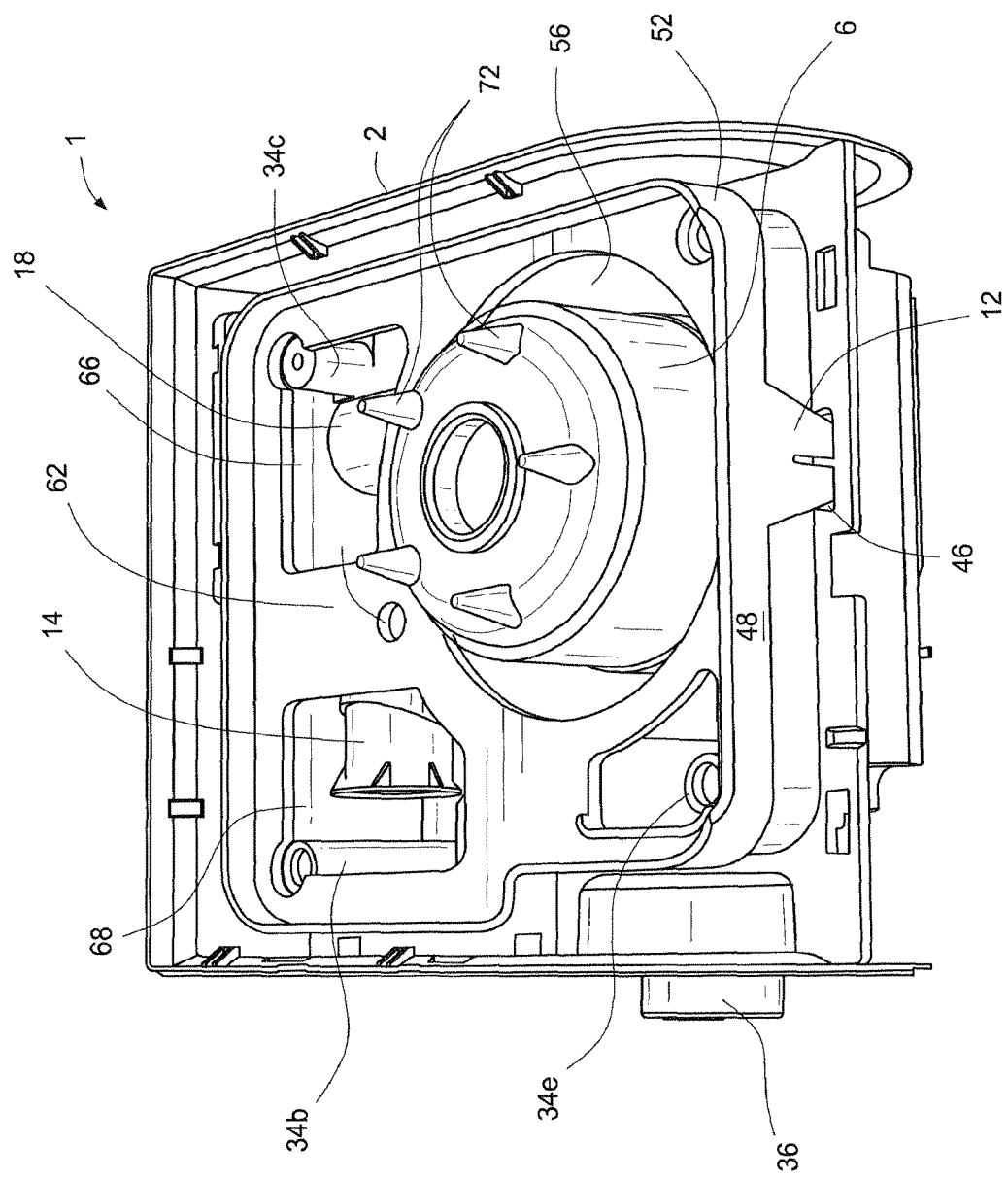
FIG. 17 is a perspective view of the flow generator seal and the upper chassis according to another sample embodiment of a method of assembly.
Figure 18:
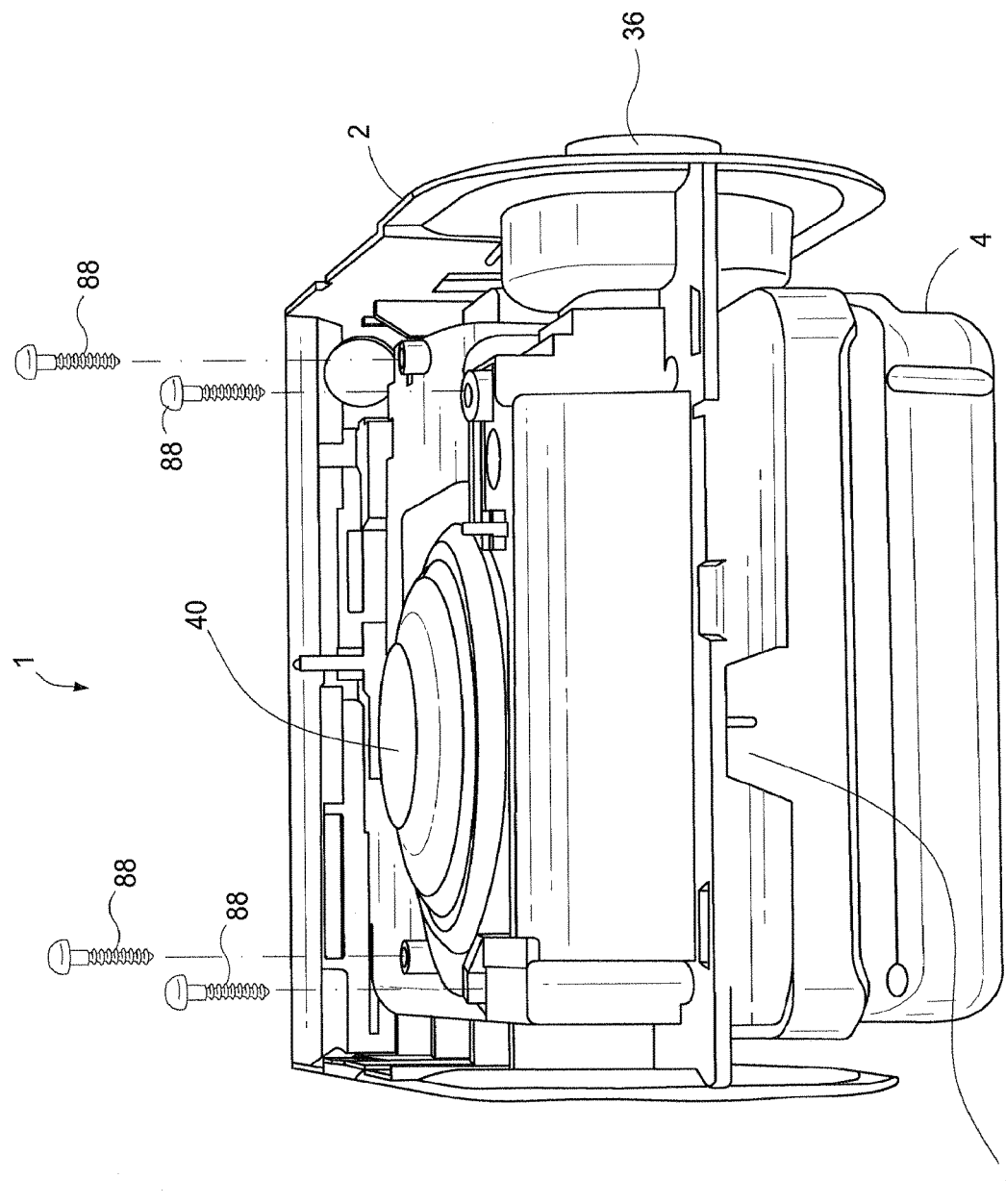
FIG. 18 is a perspective view of the flow generator prior to fastening of the upper chassis, flow generator seal, and lower chassis.

According to another sample embodiment of the assembly of the flow generator 1, the flow generator seal 6 may be assembled to the upper chassis 2 as shown in FIG. 17. The lower chassis 4 may then be assembled to the upper chassis 2 and the assembly fastened together by fasteners 88, as shown in FIG. 18.

According to another sample assembly embodiment, the upper chassis 2 is assembled with the flow tube 14. The blower 10 is then assembled with the flow generator seal 6. The wires of the motor of the blower 10 are routed through the blower wire guide 86 and the wire grommet 12 of the flow generator seal 6. The assembled flow generator seal and blower assembly 6, 10 is then aligned with the upper chassis 2 so that the wire grommet 12 aligns with the wire grommet notch 32 of the upper chassis 2. The assembled flow generator seal and blower assembly 6, 10 is then positioned on the upper chassis 2 and the flow generator seal 6 is stretched to make sure that the T-shaped skirt 48 is positioned outside the interior walls of the upper chassis 2.

The lower chassis 4 is then assembled with the foams 8, 80 and the lower chassis 4 is positioned on the flow generator seal 6. The T-shaped skirt 48 is then stretched around the perimeter 82 of the lower chassis 4 so that it fully surrounds the lower chassis 4. In an alternative embodiment, the seal may be sized to be a clearance fit over the perimeter 82 of the lower chassis 4, which may make assembly easier. The assembly is then fastened together by inserting the fasteners 88 in to the corresponding fastener receptacles 34a-34d, 78a-78d, respectively, of the upper chassis 2 and the lower chassis 4 and through the flow generator seal fastener openings 50a-50d. A fifth fastener may then be inserted into the fastener openings 34e, 78e of the upper chassis 2 and the lower chassis 4, respectively. The fifth fastener would pass through the air flow outlet seal opening 70 of the seal 6.

According to still another sample embodiment of the assembly method, the lower chassis 4 is assembled with the foams 8, 80. The blower 10 is then assembled with the flow generator seal 6 and positioned on the lower chassis 4. The T-shaped skirt 48 may be stretched so that the flow generator seal is sitting around the perimeter 82 of the lower chassis and the fastener openings 50a-50d of the flow generator seal 6 are provided around the fastener openings 78a-78d of the lower chassis 4. The wire of the motor of the blower 10 is routed through the blower wire guide 86 of the blower 10 and through the wire grommet 12 of the flow generator seal 6.

The upper chassis 2 is then assembled by securing the flow sensor 14 in to the upper chassis 2 with the flow sensor seal 16. The upper chassis 2 is then aligned with the lower chassis 4 so that the wire grommet 12 passes through the wire grommet slot 46 of the upper chassis 2 and is received in to the wire grommet notch 32 of the upper chassis 2. The assembly of the flow generator 1 is then completed by securing the fasteners 88 in to the fastener receptacles 34a-34d, 78a-78d, respectively, of the upper chassis 2 and the lower chassis 4 passing through the fastener openings 50a-50d in the flow generator seal 6. A fifth fastener may then be inserted into the fastener openings 34e, 78e of the upper chassis 2 and the lower chassis 4, respectively. The fifth fastener would pass through the air flow outlet seal opening 70 of the seal 6.

The seal mounts the motor and/or blower, provides alignment for the motor, and/or provides a suspension for the motor and/or blower. The seal also provides a seal between the high and low pressure sides of the motor and/or blower. The seal may seal the inlet air flow path and/or the outlet air flow path. The wire grommet seal seals the portion of the flow generator chassis assembly from which the wire of the motor extends. The seal also seals between acoustic chambers of the flow generator chassis assembly and/or seals the air flow path from the electronics of the flow generator. The seal may also include a flow sensor tube seal and manifold connection to the flow sensor. The provision of a seal capable of performing any or all of these functions reduces the part count and assembly time of the flow generator. The air flow path, not including the flow sensor, of the flow generator may be formed of three parts, i.e. the upper and lower chassis and the seal. The use of the upper and lower chassis along with the seal to form the air flow path allows the refinement of the upper and lower chassis, which may be formed for example of plastic, to achieve a high level of manufacturability at a lower cost.

While the technology has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A seal for a chassis assembly of a flow generator configured to provide a flow of breathable gas at a continuously positive pressure with respect to ambient air pressure to an entrance of a patient's airways, the chassis assembly including a first chassis portion and a second chassis portion, the seal comprising:

a chamber sealing portion configured to seal a plurality of chambers in the chassis assembly;
a blower mount with a central axis, the blower mount being configured to receive and support a portion of a blower configured to generate the flow of breathable gas;
a blower mount suspension configured to suspend the blower mount from the chamber sealing portion; and
a plurality of separate coplanar openings in the chamber sealing portion, each of the plurality of separate coplanar openings being configured to define a different part of an airflow path through the chamber sealing portion and enable communication of the flow of breathable gas between the plurality of chambers provided in the chassis assembly,
wherein a first opening of the plurality of separate coplanar openings is configured to receive the flow of breathable gas from a second opening of the plurality of separate coplanar openings, and
wherein a central axis of each of the plurality of separate coplanar openings is offset from the central axis of the blower mount.

2. A seal according to claim 1, further comprising a seal skirt extending around a portion of a perimeter of the seal and configured to seal a junction between the first chassis portion and the second chassis portion.

3. A seal according to claim 2, wherein at least a portion of the seal skirt has a T-shaped cross-section.

4. A seal according to claim 2, wherein a portion of the seal skirt includes an L-shaped cross-section.

5. A seal according to claim 3, wherein the T-shaped cross-section of the seal skirt does not extend around the seal in a region of an inlet of the chassis assembly, and the seal skirt has an L-shaped cross-section in the region of the inlet of the chassis assembly.

6. A seal according to claim 1, wherein the chamber sealing portion has a generally planar configuration that extends around the blower mount suspension and towards the outer perimeter of the seal.

7. A seal according to claim 6, wherein the chamber sealing portion surrounds the blower mount.

8. A seal according to claim 1, wherein the plurality of separate coplanar openings includes an inlet seal opening configured in an assembled condition to be in a region adjacent an inlet chamber of the chassis assembly.

9. A seal according to claim 1, wherein the plurality of separate coplanar openings includes a blower inlet opening configured in an assembled condition to be in a region adjacent a blower inlet chamber of the chassis assembly to allow the flow of breathable gas to enter an inlet of the blower.

10. A seal according to claim 1, wherein the plurality of separate coplanar openings include an outlet seal opening configured in an assembled condition to be in a region adjacent an outlet chamber of the chassis assembly.

11. A seal according to claim 6, wherein the chamber sealing portion further includes a flow sensor sealing portion.

12. A seal according to claim 11, wherein the flow sensor sealing portion further includes a manifold connection to the flow sensor.

13. A seal according to claim 1, further comprising:
a plurality of fastener openings configured to receive a respective plurality of fasteners configured to fasten the first chassis portion and the second chassis portion together.

14. A seal according to claim 1, wherein the blower mount suspension comprises a frusto-conical portion between the blower mount and the chamber sealing portion.

15. A seal according to claim 2, wherein the perimeter of the seal corresponds to a perimeter of the first chassis portion and/or a perimeter of the second chassis portion.

16. A seal according to claim 1, wherein the seal is formed of a flexible material.

17. A seal according to claim 1, wherein the seal is formed of an elastically deformable material.

18. A seal according to claim 1, wherein the plurality of separate coplanar openings includes at least three openings in the seal.

19. A flow generator for generating a pressurized flow of breathable gas, the flow generator comprising:
a chassis assembly comprising a first chassis portion and a second chassis portion, the first chassis portion and the second chassis portion comprising a plurality of chambers and a blower receptacle;
a blower provided in the blower receptacle; and
a seal according to claim 1.

20. A flow generator according to claim 19, wherein the plurality of chambers includes one or more of an inlet chamber, a blower inlet chamber and an outlet chamber.

21. A flow generator according to claim 20, wherein a portion of the inlet chamber is provided in both the first chassis portion and the second chassis portion and an air inlet opening in the seal enables communication within the inlet chamber between the first chassis portion and the second chassis portion and the air inlet opening is one of the openings of the plurality of separate coplanar openings in the seal.

22. A flow generator according to claim 20, wherein a portion of the outlet chamber is provided in both the first chassis portion and the second chassis portion and an air outlet opening in the seal enables communication within the outlet chamber between the first chassis portion and the second chassis portion and the air outlet opening is one of the openings of the plurality of separate coplanar openings in the seal.

23. A flow generator according to claim 20, wherein an outlet of the blower is located in the outlet chamber to receive the pressurized flow of breathable gas produced by the blower.

24. A flow generator according to claim 19, further comprising a flow sensor configured to measure the flow of breathable gas.

25. A flow generator according to claim 19, further comprising foam provided in at least one of the plurality of chambers within at least one of first chassis portion and the second chassis portion.

26. A flow generator according to claim 19, further comprising an air inlet and an air outlet provided in the first chassis portion.

27. A flow generator according to claim 19, further comprising a grommet seal configured to receive a wire of the blower.

28. A flow generator according to claim 19, wherein in use the pressurized flow of breathable gas passes through at least three openings of the plurality of separate coplanar openings in the seal between an air inlet in the chassis assembly and an air outlet in the chassis assembly.

29. A seal according to claim 1, wherein the chamber sealing portion is configured to be sandwiched between the first and second chassis portions.

30. A seal according to claim 1, wherein the blower mount is open at a first chassis portion facing side of the seal and is open at a second chassis portion facing side of the seal.

31. A flow generator according to claim 19, wherein the plurality of separate coplanar openings are positioned around the blower receptacle.

32. A seal according to claim 1, wherein the plurality of separate coplanar openings comprises openings of different chambers.

33. A seal according to claim 1, wherein the plurality of separate coplanar openings are spaced apart to sequentially receive gas flowing through the airflow path.

34. A seal according to claim 1, wherein the plurality of separate coplanar openings includes a first opening and a second opening, the first opening being configured to receive gas flowing through the airflow path before the second opening receives gas flowing through the airflow path.

35. A seal according to claim 1, wherein the plurality of separate coplanar openings includes an air inlet seal opening in the vicinity of an air inlet portion of the airflow path and an air outlet seal opening in the vicinity of an outlet of the airflow path.

36. A seal according to claim 1, wherein the central axis of each of the plurality of separate coplanar openings is parallel to the central axis of the blower mount.

* * * * *